United States Patent
Heidelbaugh et al.

(10) Patent No.: US 7,399,868 B2
(45) Date of Patent: Jul. 15, 2008

(54) 4-(HETEROARYL-METHYL AND SUBSTITUTED HETEROARYL-METHYL)-IMIDAZOLE-2-THIONES ACTING AS ALPHA2 ADRENERGIC AGONISTS

(75) Inventors: Todd M. Heidelbaugh, Fountain Valley, CA (US); Ken Chow, Newport Coast, CA (US); Phong X. Nguyen, Placentia, CA (US); Daniel W. Gil, Corona Del Mar, CA (US); John E. Donello, Dana Point, CA (US); Michael E. Garst, Newport Beach, CA (US); Larry A. Wheeler, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/232,323

(22) Filed: Sep. 20, 2005

(65) Prior Publication Data
US 2006/0069143 A1    Mar. 30, 2006

Related U.S. Application Data

(60) Provisional application No. 60/612,945, filed on Sep. 24, 2004.

(51) Int. Cl.
    C07D 233/42   (2006.01)
    C07D 403/06   (2006.01)
    C07D 209/04   (2006.01)
    C07D 209/02   (2006.01)
    C07D 487/04   (2006.01)

(52) U.S. Cl. ............ 548/311.1; 548/314.7; 548/316.4; 548/347.1; 548/468; 548/470; 548/453; 548/312.1

(58) Field of Classification Search ............ 548/311.1, 548/465, 312.1, 316.4, 348.1, 311.2, 314.7, 548/347.1, 453, 468, 470
See application file for complete search history.

(56) References Cited

U.S. PATENT DOCUMENTS

| | | | |
|---|---|---|---|
| 4,798,843 | A | 1/1989 | Kruse |
| 6,124,300 | A | 9/2000 | Rajagopalos |
| 6,486,187 | B1 | 11/2002 | Venet |

FOREIGN PATENT DOCUMENTS

| | | |
|---|---|---|
| GB | 1499485 | 2/1979 |
| JP | 06067368 | 3/1994 |
| JP | 2002097310 | 4/2002 |
| JP | 2002097312 | 4/2002 |
| WO | WO 99/28200 | 6/1999 |
| WO | WO 01/00586 | 1/2001 |
| WO | WO 02/36162 | 5/2002 |
| WO | WO 03/099795 | 12/2003 |

OTHER PUBLICATIONS

STN search report: Garcia et al. Journal of the Chemical Society, Dalton Transactions (2002), 22, p. 4236-41.*
Garcia et al., Abstract of Journal of the Chemical Society, Dalton Transactions (2002), vol. 22, p. 4236-4241.*
Ruffolo, Jr., "α-*Adrenoreceptors*": *Molecular Biology, Biochemistry and Pharmacology,* (*Progress in Basic and Clinical Pharmacology series, Karger*, 1991).
Messier et al, High Throughput Assays of Cloned Adrenergic, Muscarinic, Neurokinin, and Neurotrophin Receptors in Living Mammalian Cells, 1995, 76, pp. 308-311.
Conklin et al, "Substitution of three amino acids switches receptor specificity of Gqα to that of G1α", 1993, Nature 363: 274-6.
Dirig et al, "Characterization of variables defining hindpaw withdrawal latency evoked by radiant thermal stimuli",J. Neurosci. Methods, 1997, 76: 183-191.
Hargreaves et al, "A new and sensitive method for measuring thermal nociception in cutaneous hyperalgesia", 1988, Pain 32: 77-88.
Dixon, W.J. "Efficient Analysis of Experimental Observations", Ann. Rev. Pharmacol. Toxicol., 1980, 20: 441-462.
Minami et al, "Allodynia evoked by intrathecal administration of prostaglandin $E_2$ to conscious mice", 1994, 57 Pain, 217-223.

* cited by examiner

Primary Examiner—Joseph McKane
Assistant Examiner—Yong Chu
(74) Attorney, Agent, or Firm—Allergan, Inc.; Martin Voet; Brent A. Johnson

(57) ABSTRACT

Compounds of Formula 1

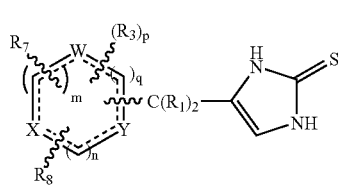

Formula 1 where the variables have the meaning defined in the specification are agonists of $alpha_2$ adrenergic receptors. Several compounds of the disclosure are specific or selective to $alpha_{2B}$ and/or $alpha_{2C}$ adrenergic receptors in preference over $alpha_{2A}$ adrenergic receptors. Additionally some of the claimed compounds have no or only minimal cardiovascular and/or sedatory activity. The compounds of Formula 1 are useful as medicaments in mammals, including humans, for treatment of diseases and or alleviations of conditions which are responsive to treatment by agonists of $alpha_2$ adrenergic receptors. Compounds of Formula 1 which have no significant cardiovascular and/or sedatory activity are useful for treating pain and other conditions with minimal side effects.

7 Claims, No Drawings

4-(HETEROARYL-METHYL AND SUBSTITUTED HETEROARYL-METHYL)-IMIDAZOLE-2-THIONES ACTING AS ALPHA2 ADRENERGIC AGONISTS

This application claims priority to Provisional Patent Application 60/612,945, filed 24 Sep. 2004, which is incorporated by reference herein.

BACKGROUND OF THE INVENTION

1. Field of the Invention

The present invention relates to 4-(heteroaryl-methyl and 4-substituted heteroaryl-methyl)-imidazole-2-thiones and to their use as agonists, preferably specific or selective agonists of alpha$_2$ adrenergic receptors. More specifically the present invention relates to the above-noted compounds, to pharmaceutical compositions containing these compounds as active ingredient for modulating the alpha2 adrenergic receptors, and even more specifically for utilizing these compounds and pharmaceutical compositions to alleviate chronic pain, allodynia, muscle spasticity, diarrhea, neuropathic pain and other diseases and conditions.

b 2. Background Art

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the $\alpha$-adrenergic receptors, the reader's attention is directed to Robert R. Ruffolo, Jr., $\alpha$-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting $\alpha$-adrenergic receptor affinity is explored.

The cloning, sequencing and expression of alpha receptor subtypes from animal tissues has led to the subclassification of the $\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha$_2$ adrenergic receptor agonist activity are known analgesics. However, many compounds having such activity do not provide the activity and specificity desirable when treating disorders modulated by alpha$_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

PCT Publication WO 03/099795 published on Dec. 4, 2003 describes 4-(substituted cycloalkylmethyl) imidazole-2-thiones, 4-(substituted cycloalkenylmethyl) imidazole-2-thiones and related compounds and their use as specific or selective agonists of alpha$_{2B}$ and/or alpha$_{2C}$ adrenergic receptors.

PCT Publication WO 02/36162 published on May 10, 2002 discloses some cyloalkenyl-methyl-imidazoles and condensed cyclic-methyl imadazoles.

Bullerwell et al. in J. Chem. Soc. 1951 3030 disclose the following compounds

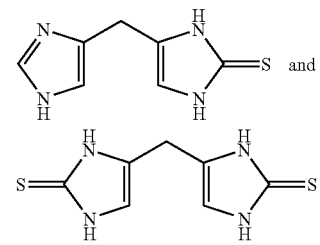

Dhanak, et al. in Bioorg. Med. Chem. Lett. 10 (2000) 2279-2282 disclose the following compounds

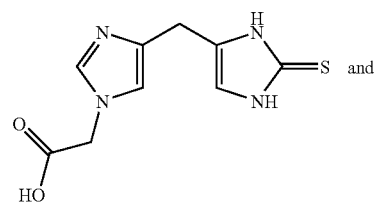

-continued

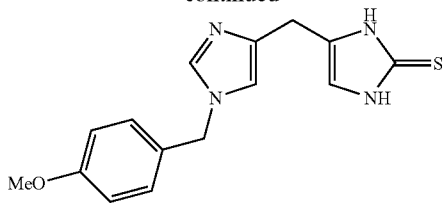

Poljakowa et al. in Zh. Obshch. Khim. 9, 1939, 1402, 1407; CHZEA6. and in Chem Zentralbl. 111; I; 1940, 869 disclose the following compound

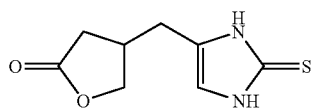

The following compounds are disclosed by the publications Prebrashenski et al. Chem Ber. 66; 1933; 1536, and Preobrashenski et al. Izv. Akad. S.S.S.R. Otd. Mat. Estestv. Ser. Chim.; 1936; 983, 992; Chem Zentrabl. GE; 108; II; 1937; 998:

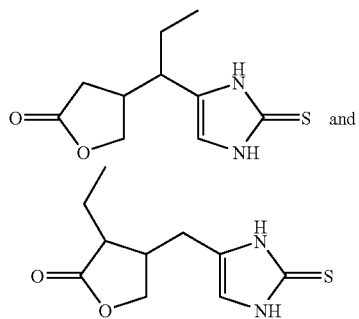

British Patent 1 499 485, published Feb. 1, 1978 describes certain thiocarbamide derivatives; some of these are said to be useful in the treatment of conditions such as hypertension, depression or pain.

PCT Publications WO01/00586 published on Jan. 4, 2001 and WO99/28300 published on Jun. 10, 1999 describe certain imidazole derivatives acting as agonists of alpha$_{2B}$ and/or alpha$_{2C}$ adrenergic receptors. U.S. Pat. No. 6,313,172 discloses phenylmethyl-thiourea derivatives used for treatment of pain.

U.S. Pat. No. 4,798,843 describes (phenyl)-imidazole-2-thiones and substituted (phenyl)-imidazole-2-thiones.

U.S. Pat. Nos. 6,124,330 and 6,486,187 describe imidazole derivatives having activity against disorders of keratinization, such as psoriasis.

Japanese Patent No. 06067368 discloses N-phenyl-imidazole-thiones. Japanese Patent Nos. 2002097310 and 2002097312 disclose additional imidazole derivatives.

U.S. Pat. Nos. 6,545,182 and 6,313,172 describe phenylmethyl-(2-hydroxy)-ethylthioureas which have no significant cardiovascular or sedative effects and are useful for alleviating chronic pain and allodynia. U.S. Pat. No. 6,534,542 describes cycloalkyl, cycloalkenyl, cycloalkylmethyl and cycloalkenylmethyl (2-hydroxy)ethylthioureas and their use as specific or selective agonists of alpha$_{2B}$ adrenergic receptors.

DESCRIPTION OF THE INVENTION

Disclosed herein are compounds of Formula 1 formula

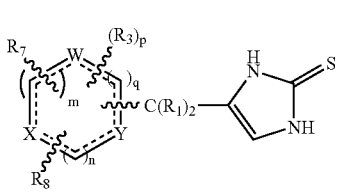

Formula 1 where m, n and q are integers selected from zero 0, 1, 2, 3 and 4 with the proviso that the sum of m, n and q is 1, 2, 3 or 4;

W, X and Y represent a carbon or a heteroatom independently selected from N, O and S with the proviso that at least one of said W, X and Y groups represents a heteroatom;

the dashed lines represent a bond or absence of a bond with the proviso that there are no more than 3 dashed lines present in the ring and with the further proviso that no dashed line representing a bond is connected to an oxygen or sulfur heteroatom;

$R_1$ is independently H, alkyl of 1 to 4 carbons, fluoro substituted alkyl of 1 to 4 carbons, $(CH_2)_sCN$, $(CH_2)_s$—$OR_2$, $(CH_2)_s$—$NR_4R_5$;

s is an integer selected from 1, 2 and 3;

$R_2$ is independently H, alkyl of 1 to 4 carbons, $C(O)R_8$, carbocyclic aryl or heterocyclic aryl having 1 to 3 heteroatoms independently selected from N, O and S;

p is an integer selected from 0, 1, 2, 3, 4 and 5;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—$CN$, $C(O)R_4$, $C(O)OR_4$, $(CH_2)_t$—$SO_2R_4$, carbocyclic aryl or heterocyclic aryl having 1 to 3 heteroatoms independently selected from N, O and S;

t is an integer selected from 0, 1, 2 and 3;

$R_4$ and $R_5$ independently are H or alkyl of 1 to 4 carbons $R_6$ is independently H, alkyl of 1 to 4 carbons, carbocyclic aryl or heterocyclic aryl having 1 to 3 heteroatoms independently selected from N, O and S;

Optionally $R_7$ and $R_8$ together with the atoms to which they are attached jointly form a carbocyclic or a heterocyclic ring, the heterocyclic ring having 5 or 6 atoms in the ring and 1 to 3 heteroatoms independently selected from N, O and S;

said carbocyclic or heterocyclic ring jointly formed by $R_7$ and $R_8$ being optionally substituted with 1 to 7 $R_9$ groups;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, C(O)OR$_6$, SO$_3$R$_6$, SO$_2$N(R$_2$)$_2$, CH$_2$SR$_2$, F, Cl, Br, I, fluoro substituted alkyl of 1 to 4 carbons, CN, N$_3$, NO$_2$, N(R$_2$)$_2$, OR$_2$, SR$_2$ or R$_8$ is O or S double bonded to one carbon of said carbocyclic or heterocyclic ring, with the proviso that the ring

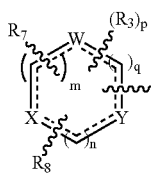

does not represent an imidazole, substituted imidazole, a 2-furanone or substituted 2-furanone.

In a second aspect the present invention is directed to pharmaceutical compositions containing as the active ingredient one or more compounds of Formula 1, the compositions being utilized as medicaments in mammals, including humans, for treatment of diseases and or alleviations of conditions which are responsive to treatment by agonists of alpha$_2$ adrenergic receptors. The compositions containing the compounds of the invention are primarily, but not exclusively, used for alleviation of chronic pain and/or allodynia. Some of the compounds of the invention have the demonstrable advantageous property that they are specific or selective to alpha$_{2B}$ and/or alpha$_{2C}$ adrenergic receptors in preference over alpha$_{2A}$ adrenergic receptors. In addition, some of the alpha 2 agonist compounds have no or only minimal cardiovascular and/or sedatory activity.

It will be readily apparent to those skilled in the art that some of the compounds depicted in the formulas disclosed herein may exist in trans (E) and cis (Z) isomeric forms. Moreover, some of the compounds of the invention may contain one or more asymmetric centers, such that the compounds may exist in enantiomeric as well as in diastereomeric forms. Unless it is specifically noted otherwise, the scope of the present invention includes all trans (E) and cis (Z) isomers, enantiomers, diastereomers and racemic mixtures. Some of the compounds of the invention may form salts with pharmaceutically acceptable acid or base, and such pharmaceutically acceptable salts of the compounds of Formula 1 are also within the scope of the invention.

The imidazole-2-thione compounds of the present invention can undergo tautomeric transformations and can be depicted by the tautomeric formulas shown below. All tautomers of Formula 1 are within the scope of the invention.

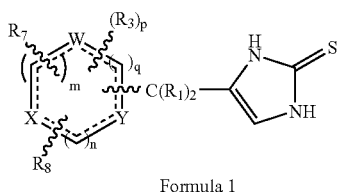

Formula 1

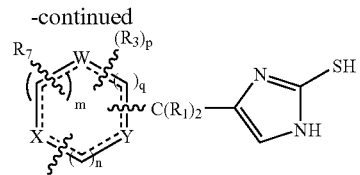

tautomeric Formula 1

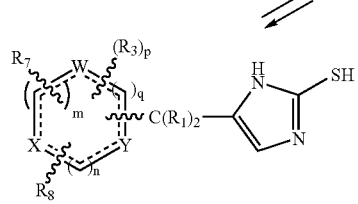

second tautomeric Formula 1

Generally speaking and referring to Formula 1, in the preferred compounds of the invention the variable R$_1$ is H, alkyl of 1 to 4 carbons, or CH$_2$OR$_2$. Even more preferably both R$_1$ groups are H, or one of the R$_1$ groups is H and the other is alkyl of 1 to 4 carbons. Still more preferably the alkyl group is methyl.

In the preferred compounds of the invention the ring, represented by Formula 1A,

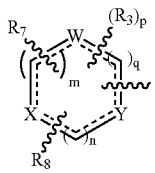

Formula 1A where the variables are defined as in connection with Formula 1, preferably is a 5 or 6 membered ring, or a 5 or 6 membered ring fused to another five or six membered ring which is represented by the variables R$_7$ and R$_8$. The five or six membered ring which is connected to the C(R$_1$)$_2$ moiety carbons ore (1) or two heteroatoms. When the heteroatom in this ring is nitrogen the C(R$_1$)$_2$ moiety may be connected to the nitrogen atom, or to a carbon atom in the ring. The ring of Formula 1A is preferably completely or partly unsaturated.

The six or 5-membered ring that may be fused to the ring of Formula 1A may contain one or two heteroatoms, or may be a carbocyclic ring. This ring may be saturated or completely or partly unsaturated. The presently preferred heteroatom in the ring which is fused to the ring of Formula 1A is nitrogen. Even more preferably the entire ring system which is connected to the C(R$_1$)$_2$ moiety is an indol, pyridinopyrrol, pyridine, thiophene, tetrahydoquinoline, cyclohexenoisoquinoline, isoquinoline, or benzofurane. Such rings are shown in the formulas of the most preferred specific compounds of the invention.

The variable p is preferably zero (0) meaning that there is no R$_3$ substituent on the ring of Formula 1A. When the variables R$_7$ and R$_8$ jointly form a ring then this ring is preferably unsubstituted or substituted with one or two R$_9$ groups which preferably are selected from the halogens, even more preferably from F, Cl and Br or from alkyls of 1 to 4 carbons. The preferred alkyl substituent in this regard is methyl.

Another embodiment is a compound of the structure

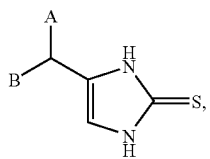

wherein A is H or methyl, and
B is monocyclic or bicyclic heteroaryl having 0, 1, or 2 substituents,
wherein each substituent is independently Cl, Br, F, or methyl.

Since A is H or methyl, structures such as those shown below are contemplated.

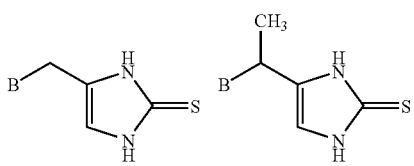

Monocyclic or bicyclic heteroaryl is a monocyclic or bicyclic ring system wherein at least one of the rings is heteroaryl. Monocyclic heteroaryl is a single aromatic ring with a heteroatom. Examples of monocyclic heteroaryl include pyridinyl, thienyl, furyl, and the like. Bicyclic heteroaryl is a bicyclic structure wherein at least one of the rings, if considered individually, is monocyclic heteroaryl. Examples of bicyclic heteroaryl include indolyl, quinolinyl, isoquinolinyl, benzothienyl, and the like. Bicyclic heteroaryl may also be a ring system wherein both rings have a heteroatom. For example, both rings may contain nitrogen.

In one embodiment B is indolyl having a single substituent.

In another embodiment B is pyridinyl having a single substituent.

The presently most preferred compounds of the invention are disclosed by their structural formulas in Table 1 together with their activity in assays measuring their ability to act as agonists of alpha$_{2A}$, alpha$_{2B}$ and alpha$_{2C}$ adrenergic receptors.

TABLE 1

| Biological Data: Intrinsic Activity | | | |
|---|---|---|---|
| Structure | Alpha 2A | Alpha 2B | Alpha 2C |
| Compound 1 | NA | 1.17 | NA |
| Compound 2 | NA | 1.01 | NA |
| Compound 3 | NA | 1.07 | NA |
| Compound 4 | NA | 1.17 | NA |
| Compound 5 | NA | 1.01 | 0.77 |
| Compound 6 | NA | 0.98 | NA |
| Compound 7 | NA | 1.5 | NA |
| Compound 8 | NA | 0.76 | NA |
| Compound 9 | NA | 1.16 | NA |

TABLE 1-continued

Biological Data: Intrinsic Activity

| Structure | Alpha 2A | Alpha 2B | Alpha 2C |
|---|---|---|---|
| Compound 10 | NA | 1.09 | NA |
| Compound 11 | NA | 1.13 | NA |
| Compound 12 | NA | 0.99 | NA |
| Compound 13 | NA | 0.77 | NA |
| Compound 14 | NA | 1.0 | NA |

General Methods for Obtaining the Compounds of the Invention

Reaction Schemes A-C illustrate general methods for obtaining the 4-(heterocyclyl)-imidazole-2-thiones.

Reaction Scheme A employs an aldehyde or ketone starting material of Formula 2 which can be obtained through commercial sources or prepared in accordance with known procedures in the chemical scientific and patent literature or by modifications of known procedures which are readily apparent to the practicing synthetic organic chemist. The variables in Formula 2 are defined as in connection with Formula 1. The aldehyde or ketone of Formula 2 is reacted with a Grignard reagent of 4-iodo-1-trityl-1H-imidazole to provide the triphenylmethyl (trityl)-protected hydroxyimidazole compounds of Formula 3. Deoxygenation of the bridging hydroxyl moiety was accomplished by methods such as treatment with trifluoroacetic acid in triethyl silane or, if the staring material was an aldehyde by oxidation of the alcohol to a ketone which can be reduced with a Huang-Minlon modification of the Wolff-Kishner reduction, followed by acidic deprotection of the trityl group to produce imidazoles of Formula 4. The imidazoles of Formula 4 are reacted with phenyl chlorothionoformate in the presence of sodium bicarbonate and water and subsequently treated with a base, such as triethylamine to produce 4-(heterocyclyl)-imidazole-2-thiones. of Formula 5. The compounds of Formula 5 are within the scope of the invention.

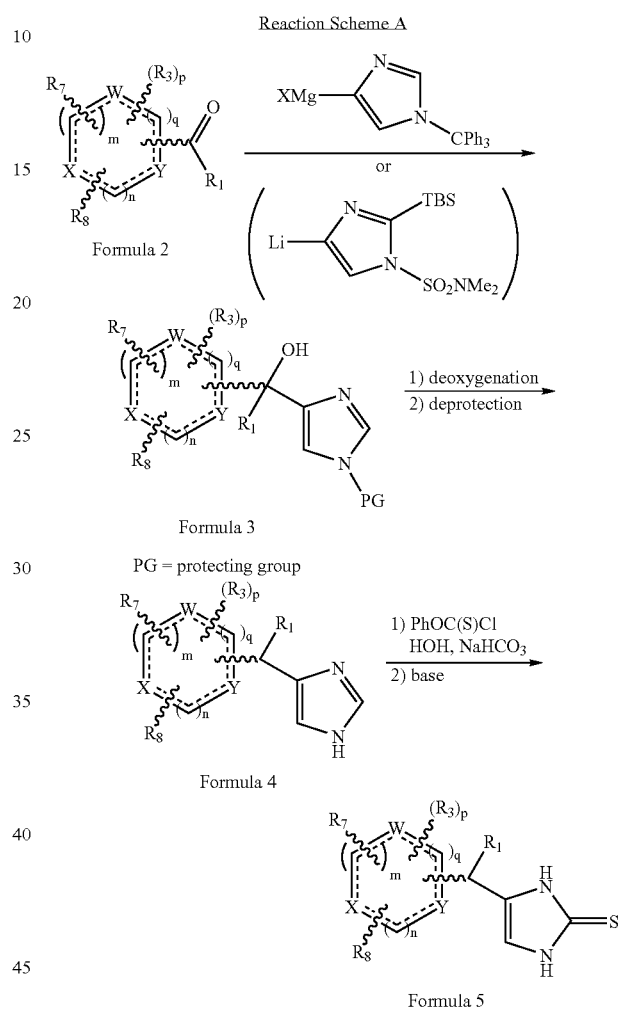

Reaction Scheme B describes another general method for the preparation of 4-(heterocyclyl)-imidazole-2-thiones of Formula 9 wherein one of the $R_1$ groups is H and the other is an alkyl group, preferably methyl. In this scheme Compounds of Formula 3, as prepared in Reaction Scheme A and obtained from an aldehyde of Formula 2, are oxidized to the ketones of Formula 6. Addition of a Grignard reagent $R_1$MgBr produces tertiary alcohols of Formula 7. (Alternatively, compounds of Formula 7 can be prepared by use of a ketone starting material in the addition step as per Reaction Scheme A.) Deoxygenation of the tertiary alcohols is conducted via an elimination/reduction methodology, and removal of the trityl protecting group is accomplished under acidic conditions to deliver imidazole compounds of Formula 8. The imidazoles of Formula 8 are reacted with phenylchlorothionoformate in the presence of sodium bicarbonate and water and subsequently treated with a base, such as triethylamine to produce 4-(heterocyclyl)-imidazole-2-thiones of Formula 9. The compounds of Formula 9 are within the scope of the invention.

Reaction Scheme B

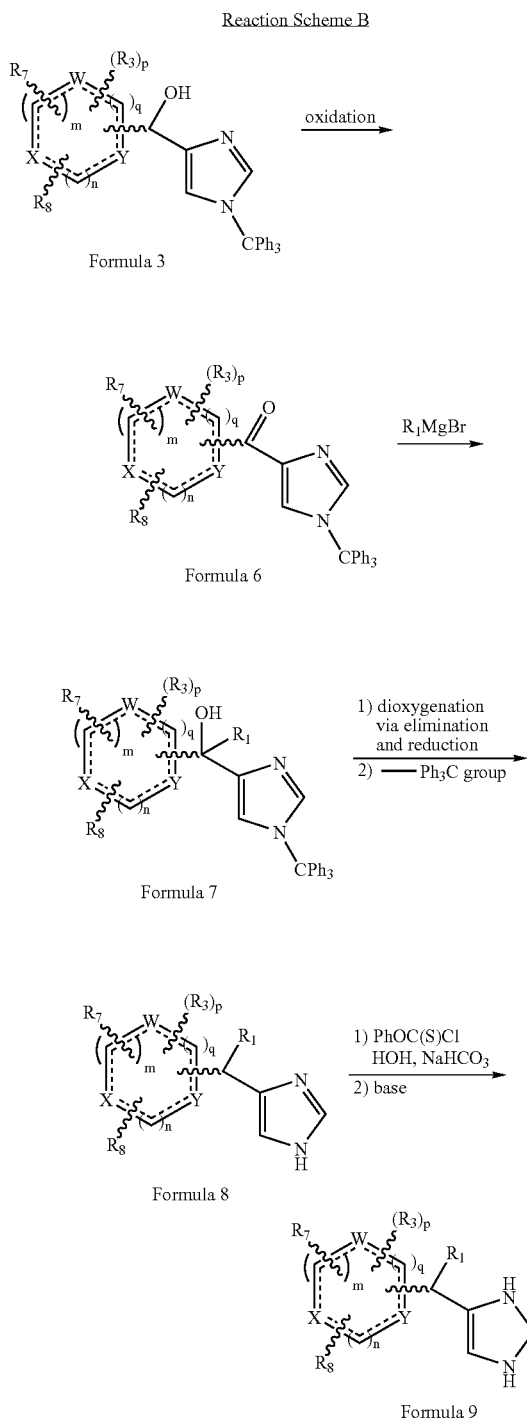

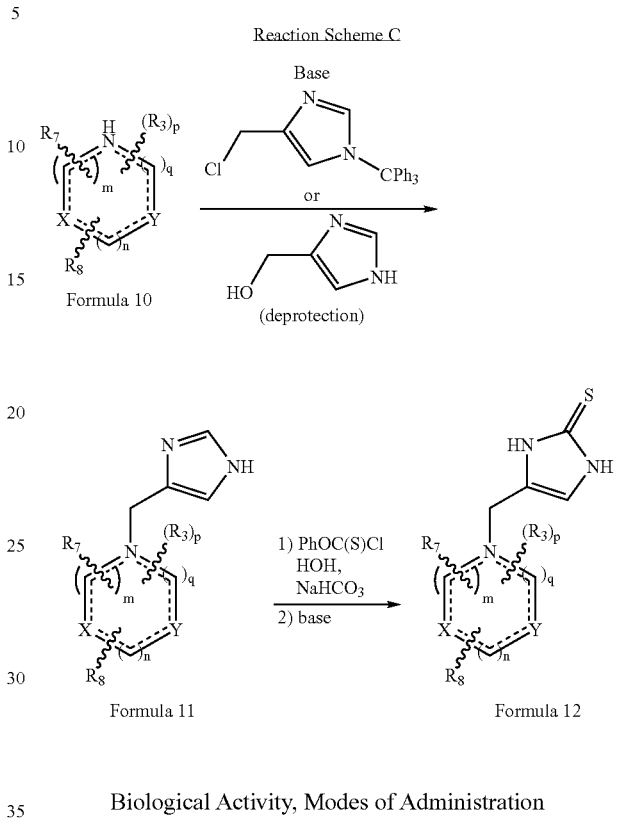

Reaction Scheme C employs an amine starting material of Formula 10 which can be obtained through commercial sources or prepared in accordance with known procedures in the chemical scientific and patent literature or by modifications of known procedures which are readily apparent to the practicing synthetic organic chemist. The amine of Formula 10 is reacted with a base such as potassium hydroxide or sodium carbonate and 4-chloromethyl-1-trityl-imidazole or 4-hydroxymethyl-imidazole and thereafter deprotected to produce the imidazole compounds of Formula 11. The imidazoles of Formula 11 were reacted with phenychlorothionoformate as described above to obtain compounds of Formula 12.

Biological Activity, Modes of Administration

The imidazole-2-thione compounds of the invention are agonists of alpha$_2$ adrenergic receptors. The alpha$_2$ receptor activity of the compounds of the invention is demonstrated in an assay titled Receptor Selection and Amplification technology (RSAT) assay, which is described in the publication by Messier et. Al., 1995, Pharmacol. Toxicol. 76, pp. 308-311 (incorporated herein by reference) and is also described below. Another reference pertinent to this assay is Conklin et al. (1993) Nature 363:274-6, also incorporated herein by reference.

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as $\exists$-galactosidase, the activity of which can be easily measured in a 96-well format. Receptors that activate the G protein, $G_q$, elicit this response. Alpha2 receptors, which normally couple to $G_i$, activate the RSAT response when coexpressed with a hybrid $G_q$ protein that has a $G_i$ receptor recognition domain, called $G_q/i5$.

NIH-3T3 cells are plated at a density of $2 \times 10^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 µl added to 100 µl aliquots of various concentrations of drugs in triplicate in 96-well dishes. Incubations continue 72-96 hr at 37° C. After washing with phosphate-buffered saline, β-galactosidase enzyme activity is determined by adding 200 µl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the $alpha_{2A}$, $alpha_{2B}$ and $alpha_{2C}$ receptors.

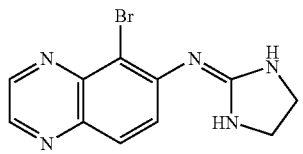

brimonidine

Diseases that may be treated with this invention include, but are not limited to neurodegenerative aspects of the following conditions:

MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, UVEITIS/RETINITIS/CHOROIDITIS/OTHER INFLAMMATORY DISEASES Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy VASUCLAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The results of the RSAT assay with several exemplary compounds of the invention are disclosed in Table 1 above together with the chemical formulas of these examplary compounds. NA stands for "not active" at concentrations less than 10 micromolar.

Generally speaking $alpha_2$ agonists, can alleviate sympathetically-sensitized conditions that are typically associated with periods of stress. These include the neurological conditions of 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

$Alpha_2$ agonists including $alpha_{2B/2C}$ agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of alpha$_{2B}$ and/or alpha$_{2C}$ adrenergic receptors in preference over alpha$_{2A}$ receptors, if the compound is more active, preferably at least ten (10) times more active towards either alpha$_{2B}$ or towards alpha$_{2C}$ receptors than towards alpha$_{2A}$ receptors. It can be seen from these tables that several compounds of the invention are specific or selective agonists of alpha$_{2B}$ and/or alpha$_{2C}$ adrenergic receptors within the former definition, and in have no agonist like activity or only insignificant agonist-like activity on alpha$_{2A}$ receptors. However, compounds of the invention which are active as agonists of all three alpha$_2$ receptors (pan agonists) are also desirable.

Thus, the imidazole-2-thione compounds of the invention are useful for treating conditions and diseases which are responsive to treatment by alpha$_2$B and particularly by alpha$_{2B}$ and/or alpha$_{2C}$ adrenergic receptor agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds of this invention are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis.

The activity of the compounds of the invention is highly advantageous because the administration of these compounds to mammals does not result in sedation or in significant cardiovascular effects (such as changes in blood pressure or heart rate).

The compounds of the invention act and can be used as a highly effective analgesic, particularly in chronic pain models, with minimal undesirable side effects, such as sedation and cardiovascular depression, commonly seen with other agonists of the alpha$_2$ receptors.

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the invention is drawn to therapeutic compositions comprising the compounds of Formula 1 and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more compounds of Formula 1 or pharmaceutically acceptable salts thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) are distinct neurological phenomena mediated to a large degree either by different nerve fibers and neuroreceptors or by a rearrangement or alteration of the function of these nerves upon chronic stimulation. Sensation of acute pain is transmitted quite quickly, primarily by afferent nerve fibers termed C fibers, which normally have a high threshold for mechanical, thermal, and chemical stimulation. While the mechanisms of chronic pain are not completely understood, acute tissue injury can give rise within minutes or hours after the initial stimulation to secondary symptoms, including a regional reduction in the magnitude of the stimulus necessary to elicit a pain response. This phenomenon, which typically occurs in a region emanating from (but larger than) the site of the original stimulus, is termed hyperalgesia. The secondary response can give rise to profoundly enhanced sensitivity to mechanical or thermal stimulus.

The A afferent fibers (A∃ and A* fibers) can be stimulated at a lower threshold than C fibers, and appear to be involved in the sensation of chronic pain. For example, under normal conditions, low threshold stimulation of these fibers (such as a light brush or tickling) is not painful. However, under certain conditions such as those following nerve injury or in the herpes virus-mediated condition known as shingles the application of even such a light touch or the brush of clothing can be very painful. This condition is termed allodynia and appears to be mediated at least in part by A∃ afferent nerves. C fibers may also be involved in the sensation of chronic pain, but if so it appears clear that persistent firing of the neurons over time brings about some sort of change which now results in the sensation of chronic pain.

By "acute pain" is meant immediate, usually high threshold, pain brought about by injury such as a cut, crush, burn, or by chemical stimulation such as that experienced upon exposure to capsaicin, the active ingredient in chili peppers.

By "chronic pain" is meant pain other than acute pain, such as, without limitation, neuropathic pain, visceral pain (including that brought about by Crohn's disease and irritable bowel syndrome (IBS)), and referred pain.

Specifically Contemplated Embodiments

In addition to those compounds, methods, and compositions disclosed herein, the embodiments disclosed below are specifically contemplated.

Compound Embodiments

One embodiment is a compound of the formula

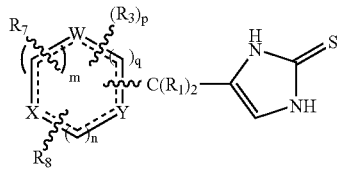

where m, n and q are integers selected from zero 0, 1, 2, 3 and 4 with the proviso that the sum of m, n and q is 1, 2, 3 or 4;

W, X and Y represent a carbon or a heteroatom independently selected from N, O and S with the proviso that at least one of said W, X and Y groups represents a heteroatom;

the dashed lines represent a bond or absence of a bond with the proviso that there are no more than 3 dashed lines present in the ring and with the further proviso that no dashed line representing a bond is connected to an oxygen or sulfur heteroatom;

$R_1$ is independently H, alkyl of 1 to 4 carbons, fluoro substituted alkyl of 1 to 4 carbons, $(CH_2)_sCN$, $(CH_2)_s$—$OR_2$, $(CH_2)_s$—$NR_4R_5$;

s is an integer selected from 1, 2 and 3;

$R_2$ is independently H, alkyl of 1 to 4 carbons, $C(O)R_8$, carbocyclic aryl or heterocyclic aryl having 1 to 3 heteroatoms independently selected from N, O and S;

p is an integer selected from 0, 1, 2, 3, 4 and 5;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—$CN$, $C(O)R_4$, $C(O)OR_4$, $(CH_2)_t$—$SO_2R_4$, carbocyclic aryl or heterocyclic aryl having 1 to 3 heteroatoms independently selected from N, O and S;

t is an integer selected from 0, 1, 2 and 3;

$R_4$ and $R_5$ independently are H or alkyl of 1 to 4 carbons $R_6$ is independently H, alkyl of 1 to 4 carbons, carbocyclic aryl or heterocyclic aryl having 1 to 3 heteroatoms independently selected from N, O and S;

Optionally $R_7$ and $R_8$ together with the atoms to which they are attached jointly form a carbocyclic or a heterocyclic ring, the heterocyclic ring having 5 or 6 atoms in the ring and 1 to 3 heteroatoms independently selected from N, O and S;

said carbocyclic or heterocyclic ring jointly formed by $R_7$ and R, being optionally substituted with 1 to 7 $R_9$ groups;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, $SR_2$ or $R_8$ is O or S double bonded to one carbon of said carbocyclic or heterocyclic ring, with the proviso that the ring

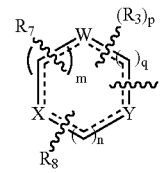

does not represent an imidazole, substituted imidazole, a 2-furanone or substituted 2-furanone.

Another embodiment is compound having the formula

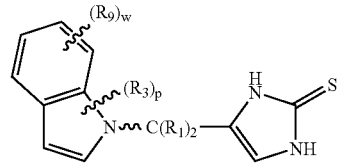

wherein $R_1$ is independently H, alkyl of 1 to 4 carbons, fluoro substituted alkyl of 1 to 4 carbons, $(CH_2)_sCN$, $(CH_2)_s$—$OR_2$, $(CH_2)_s$—$NR_4R_5$;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—$CN$, $C(O)R_4$, $C(O)OR_4$, $(CH_2)_t$—$SO_2R_4$, carbocyclic aryl or heterocyclic aryl having 1 to 3 heteroatoms independently selected from N, O and S;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, and $SR_2$;

w is 0, 1, 2, 3 or 4; and p is 0, 1 or 2.

In another embodiment $R_9$ is selected from the group consisting of F, Cl, Br and methyl and w is 1 or 2.

In another embodiment both $R_1$ groups are H.

Another embodiment is a compound having the formula

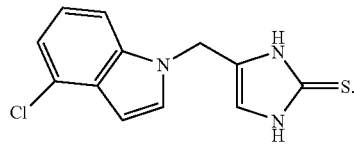

Another embodiment is a compound having the formula

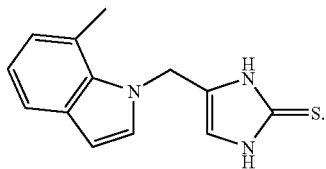

Another embodiment is a compound having the formula

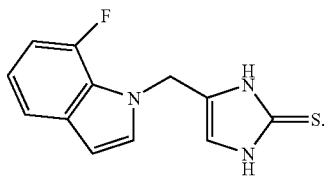

Another embodiment is a compound having the formula

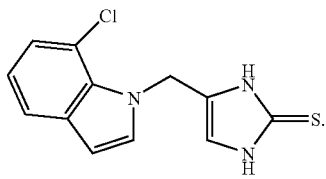

Another embodiment is a compound having the formula

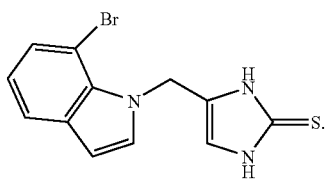

Another embodiment is a compound having the formula

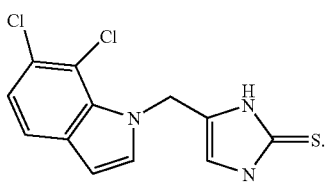

Another embodiment is a compound having the formula

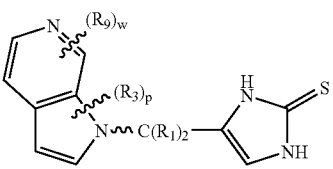

wherein $R_1$ is independently H, alkyl of 1 to 4 carbons, fluoro substituted alkyl of 1 to 4 carbons, $(CH_2)_s CN$, $(CH_2)_s$—$OR_2$, $(CH_2)_s$—$NR_4R_5$;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—$CN$, $C(O)R_4$, $C(O)OR_4$, $(CH_2)_t$—$SO_2R_4$, carbocyclic aryl or heterocyclic aryl having 1 to 3 heteroatoms independently selected from N, O and S;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, and $SR_2$;

w is 1, 2, 3 or 4; and p is 0, 1 or 2.

In another embodiment $R_9$ is selected from the group consisting of F, Cl, Br and methyl and w is 1 or 2.

In another embodiment both $R_1$ groups are H.

Another embodiment is a compound having the formula

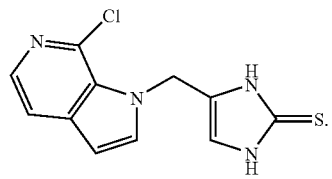

Another embodiment is a compound having the formula

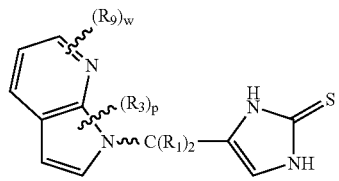

wherein $R_1$ is independently H, alkyl of 1 to 4 carbons, fluoro substituted alkyl of 1 to 4 carbons, $(CH_2)_s CN$, $(CH_2)_s$—$OR_2$, $(CH_2)_s$—$NR_4R_5$;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—$CN$, $C(O)R_4$, $C(O)OR_4$, $(CH_2)_t$—$SO_2R_4$, carbocyclic aryl or heterocyclic aryl having 1 to 3 heteroatoms independently selected from N, O and S;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, and $SR_2$;

w is 1, 2, 3 or 4; and p is 0, 1 or 2.

In another embodiment R$_9$ is selected from the group consisting of F, Cl, Br and methyl and w is 1 or 2.

In another embodiment both R$_1$ groups are H.

Another embodiment is a compound having the formula

Another embodiment is a compound having the formula wherein R$_1$ is independently H, alkyl of 1 to 4 carbons, fluoro substituted alkyl of 1 to 4 carbons, (CH$_2$)$_s$CN, (CH$_2$)$_s$—OR$_2$, (CH$_2$)$_s$—NR$_4$R$_5$;

R$_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, N$_3$, NO$_2$, (CH$_2$)$_t$—OR$_2$, (CH$_2$)$_t$—NR$_5$R$_6$, (CH$_2$)$_t$—CN, C(O)R$_4$, C(O)OR$_4$, (CH$_2$)$_t$—SO$_2$R$_4$, carbocyclic aryl or heterocyclic aryl having 1 to 3 heteroatoms independently selected from N, O and S; and p is an integer selected from 0, 1, 2, 3, 4 and 5.

In another embodiment R$_3$ is selected from the group consisting of F, Cl, Br and methyl and p is 0, 1 or 2.

In another embodiment both R$_1$ groups are H.

Another embodiment is a compound having the formula

Another embodiment is a compound having the formula wherein R$_1$ is independently H, alkyl of 1 to 4 carbons, fluoro substituted alkyl of 1 to 4 carbons, (CH$_2$)$_s$CN, (CH$_2$)$_s$—OR$_2$, (CH$_2$)$_s$—NR$_4$R$_5$;

R$_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, N$_3$, NO$_2$, (CH$_2$)$_t$—OR$_2$, (CH$_2$)$_t$—NR$_5$R$_6$, (CH$_2$)$_t$—CN, C(O)R$_4$, C(O)OR$_4$, (CH$_2$)$_t$—SO$_2$R$_4$, carbocyclic aryl or heterocyclic aryl having 1 to 3 heteroatoms independently selected from N, O and S; and p is an integer selected from 0, 1, 2, 3, 4 and 5.

In another embodiment R$_3$ is selected from the group consisting of F, Cl, Br and methyl.

In another embodiment both R$_1$ groups are H.

Another embodiment is a compound having the formula

Another embodiment is a compound having the formula wherein R$_1$ is independently H, alkyl of 1 to 4 carbons, fluoro substituted alkyl of 1 to 4 carbons, (CH$_2$)$_s$CN, (CH$_2$)$_s$—OR$_2$, (CH$_2$)$_s$—NR$_4$R$_5$;

R$_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, N$_3$, NO$_2$, (CH$_2$)$_t$—OR$_2$, (CH$_2$)$_t$—NR$_5$R$_6$, (CH$_2$)$_t$—CN, C(O)R$_4$, C(O)OR$_4$, (CH$_2$)$_t$—SO$_2$R$_4$, carbocyclic aryl or heterocyclic aryl having 1 to 3 heteroatoms independently selected from N, O and S;

R$_9$ is independently selected from the groups consisting of alkyl of 1 to 4 carbons, alkenyl of 2 to 4 carbons, alkynyl of 2 to 4 carbons, CH$_2$OR$_2$, CH$_2$N(R$_2$)$_2$, CH$_2$CN, C(O)R$_2$, C(O)OR$_6$, SO$_3$R$_6$, SO$_2$N(R$_2$)$_2$, CH$_2$SR$_2$, F, Cl, Br, I, fluoro substituted alkyl of 1 to 4 carbons, CN, N$_3$, NO$_2$, N(R$_2$)$_2$, OR$_2$, and SR$_2$;

p is an integer selected from 0, 1, 2, 3, 4 and 5; and w is 1, 2, 3 or 4.

In another embodiment R$_9$ is selected from the group consisting of F, Cl, Br and methyl and w is 1 or 2.

In another embodiment both R$_1$ groups are H.

Another embodiment is a compound having the formula

Another embodiment is a compound having the formula wherein R₁ is independently H, alkyl of 1 to 4 carbons, fluoro substituted alkyl of 1 to 4 carbons, $(CH_2)_sCN$, $(CH_2)_s$—$OR_2$, $(CH_2)_s$—$NR_4R_5$;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—CN, $C(O)R_4$, $C(O)OR_4$, $(CH_2)_t$—$SO_2R_4$, carbocyclic aryl or heterocyclic aryl having 1 to 3 heteroatoms independently selected from N, O and S;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, and $SR_2$;

p is an integer selected from 0, 1, 2, 3, 4 and 5; and
w is 1, 2, 3 or 4.

In another embodiment $R_9$ is selected from the group consisting of F, Cl, Br and methyl and w is 1 or 2.

In another embodiment one $R_1$ group is H, and the other is alkyl of 1 to 4 carbons.

Another embodiment is a compound having the formula

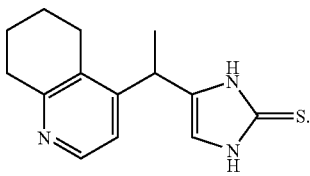

Another embodiment is a compound having the formula

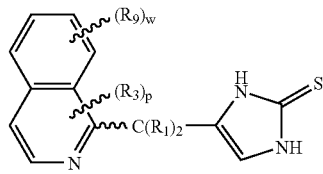

wherein R₁ is independently H, alkyl of 1 to 4 carbons, fluoro substituted alkyl of 1 to 4 carbons, $(CH_2)_sCN$, $(CH_2)_s$—$OR_2$, $(CH_2)_s$—$NR_4R_5$;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—CN, $C(O)R_4$, $C(O)OR_4$, $(CH_2)_t$—$SO_2R_4$, carbocyclic aryl or heterocyclic aryl having 1 to 3 heteroatoms independently selected from N, O and S;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, and $SR_2$;

w is 1, 2, 3 or 4; and
p is 0, 1 or 2.

In another embodiment $R_9$ is selected from the group consisting of F, Cl, Br and methyl and w is 1 or 2.

In another embodiment one $R_1$ group is H and the other is alkyl of 1 to 4 carbons.

Another embodiment is a compound having the formula

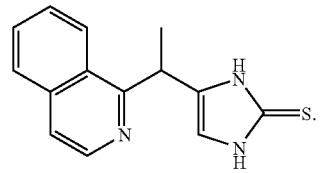

Another embodiment is a compound having the formula

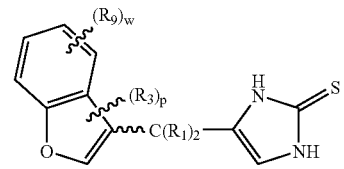

wherein R₁ is independently H, alkyl of 1 to 4 carbons, fluoro substituted alkyl of 1 to 4 carbons, $(CH_2)_sCN$, $(CH_2)_s$—$OR_2$, $(CH_2)_s$—$NR_4R_5$;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_t$—$OR_2$, $(CH_2)_t$—$NR_5R_6$, $(CH_2)_t$—CN, $C(O)R_4$, $C(O)OR_4$, $(CH_2)_t$—$SO_2R_4$, carbocyclic aryl or heterocyclic aryl having 1 to 3 heteroatoms independently selected from N, O and S;

$R_9$ is independently selected from the groups consisting of alkyl of 1 to 4 carbons, alkenyl of 2 to 4 carbons, alkynyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $NO_2$, $N(R_2)_2$, $OR_2$, and $SR_2$;

w is 1, 2, 3 or 4; and
p is 0, 1 or 2.

In another embodiment $R_9$ is selected from the group consisting of F, Cl, Br and methyl and w is 1 or 2.

In another embodiment one $R_1$ group is H and the other is alkyl of 1 to 4 carbons.

Another embodiment is a compound having the formula

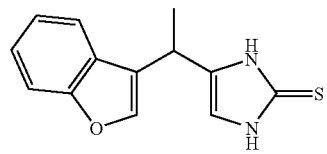

In another embodiment, the ring

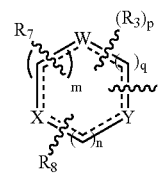

is 5-membered.

In another embodiment, the ring

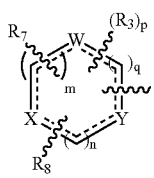

has one heteroatom.

In another embodiment, the ring

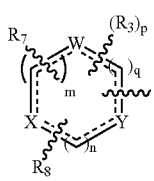

is 6-membered.

In another embodiment, the ring

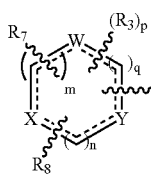

has one heteroatom which is N.

In another embodiment, $R_7$ and $R_8$ do not represent a ring fused to the ring

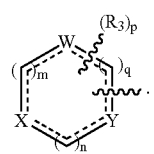

In another embodiment, $R_7$ and $R_8$ represent a ring fused to the ring

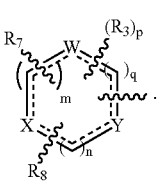

Method Embodiments

Another embodiment is a method of activating alpha$_{2B}$ or alpha$_{2C}$ adrenergic receptors in a mammal in need of such activation by administering to the mammal a pharmaceutical composition containing a therapeutically effective dose of a compound in accordance with claim 1.

Another embodiment is a method where the pharmaceutical composition is administered to the mammal to alleviate pain.

Another embodiment is a method where the pharmaceutical composition is administered to the mammal to alleviate chronic pain.

Another embodiment is a method where the pharmaceutical composition is administered to the mammal to alleviate allodynia.

Another embodiment is a method where the pharmaceutical composition is administered orally.

Another embodiment is a method where the pharmaceutical composition is administered intraperitonially.

Another embodiment is a method where the mammal is administered the composition for treating a condition selected from the group consisting of chronic pain, visceral pain, neuropathic pain, corneal pain, glaucoma, elevated intraocular pressure, ischemic neuropathies, neurodegenerative diseases, diarrhea, nasal congestion, muscle spasticity, diuresis, withdrawal syndromes, neurodegenerative diseases, optic neuropathy, spinal ischemia, stroke, memory and cognition deficits, attention deficit disorder, psychoses, manic disorders, anxiety, depression, hypertension, congestive heart failure, cardiac ischemia, arthritis, spondylitis, gouty arthritis, osteoarthritis, juvenile arthritis, autoimmune diseases, lupus erythematosus, chronic gastrointestinal inflammations, Crohn's disease, gastritis, irritable bowel syndrome (IBS), functional dyspepsia and ulcerative colitis.

Another embodiment is a method where the mammal is administered the composition for treating glaucoma.

Another embodiment is a method where the mammal is administered the composition for treating neuropathies or neurodegenerative diseases.

Another embodiment is a method where the mammal is administered the composition for treating muscle spasticity.

The following in vivo assays can be employed to demonstrate the biological activity of the compounds of the invention.

Sedative Activity

To test sedation, six male Sprague-Dawley rats are given up to 3 mg/kg of the test compound in a saline or DMSO vehicle by intraperitoneal injection (i.p.). Sedation is graded 30 minutes following administration of the drug by monitoring locomotor skills as follows.

The Sprague-Dawley rats are weighed and 1 ml/kg body weight of an appropriate concentration (ie. 3 mg/ml for a final dose of 3 mg/kg) drug solution is injected intraperitoneally. Typically the test compound is formulated in approximately 10 to 50% DMSO. The results are compared to controls that are injected with 1 ml/kg saline or 10 to 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation.

Representative Compounds 3 and 5 of the invention were tested in this assay intraperitoneally and up to a dose of 1 mg/kg, and were found to have no sedative effect. The results in this test with other compounds of the invention are also expected to show that the compounds of the invention have no significant sedatory activity.

Effects on Cardiovascular System

To test the effect of the compounds on the cardiovascular system, typically six cynomolgus monkeys are given 500 μg/kg of the test compound by intravenous injection (i.v.) Or 3 mg/kg by oral gavage. The effects of the compound on the animals' blood pressure and heart rate is measured at time intervals from 30 minutes to six hours following administration of the drug. The peak change from a baseline measurement taken 30 minutes before drug administration is recorded using a blood pressure cuff modified for use on monkeys.

Specifically and typically the monkeys are weighed (approximately 4 kg) and an appropriate volume (0.1 ml/kg) of a 5 mg/ml solution of the test compound formulated in 10 to 50% DMSO is injected into the cephalic vein in the animals' arm. Cardiovascular measurements are made with a BP 100S automated sphygmomanometer (Nippon Colin, Japan) at 0.5, 1, 2, 4 and 6 hours.

The results of this test show that the compounds of the invention are expected to have no or only minimal detectable effect on the cardiovascular system.

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183-191 (1997) and Hargreaves, K. et al., *Pain* 32:77-88 (1988), hereby incorporated by reference herein.

In a variation of this latter model, male Sprague-Dawley rats are tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after 20 seconds to prevent tissue damage.

Typically four test animals per group are weighed (approximately 0.3 kg) and injected intraperitonealy (i.p.) with 1 ml/kg of the test compound formulated in approximately 10 to 50% dimethylsulfoxide (DMSO) vehicle. Animals typically receive a 0.1 mg/kg and a 1 mg/kg dose of the three compounds. Rats are acclimated to the test chamber for about 15 minutes prior to testing. The paw withdrawal latency is measured at 30, 60 and 120 minutes after drug administration. The right and left paws are tested 1 minute apart, and the response latencies for each paw are averaged. Stimulus intensity is sufficient to provide a temperature of 45-50 degrees centigrade to each rat hindpaw.

The results in this test are expected to show that the compounds of the invention which are selective or specific for alpha$_{2B}$ and/or alpha 2c receptors do not provide analgesic effects in this bioassay of acute pain.

Alleviation of Chronic Pain

A model in accordance with Kim and Chung 1992, Pain 150, pp 355-363 (Chung model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in d H$_2$O and given in a volume of 1 ml/kg body weight using an 18-gauge, 3 inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. The post-drug threshold is compared to the pre-drug threshold and the percent reversal of tactile sensitivity is calculated based on a normal threshold of 15.1 grams.

Table 3 below indicates results of this test with Compound 14 of the invention, administered i.p. and in oral doses. The doses and the observed MPE values (±SEM) are shown in the table.

TABLE 3

| | Activity of Compounds in Chung Model of Neuropathic Pain (% Pain Reversal) | |
|---|---|---|
| Compd. | 30 µg/kg i.p. | 300 µg/kg i.p. |
| 14 | 20 | 80 |

All measurements 30 min following drug administration.
p value<0.001 compared to pretreatment values.

The Mouse Sulprostone Model is an alternative model in which chronic pain, allodynia can be induced in mice through intrathecal treatment of the animals with 200 ng sulprostone (prostaglandin E2 receptor agonist) in 50% DMSO and in volume of 5 µl. In this model, the pain response to stroking the flank with a paint brush is scored 8 times over a 35 minute period starting 15 minutes following final administration of suiprostone. Minami et al., 57 Pain 217-223 (1994), hereby incorporated by reference. Sulprostone treatment alone elicits a score of 12-13 on a 16- point scale.

In variants of this model, allodynia can be induced using intraperitoneal injection of 300 µg/kg sulprostone or 30 µg/kg phenylephrine. Alternatively allodynia can be induced using intrathecal injection of 100 ng N-methyl-D-asparate (NMDA) or 30 ng phenylephrine (PE) formulated in dH$_2$O in a volume of e. g. 5 microliters.

In either model, the compounds are formulated in dH$_2$O and given in a volume of 1 ml/kg body weight for intraperitoneal (IP) dosing.

The results shown in Table 3 illustrate that these compounds of the invention significantly alleviate allodynic pain, and based on these test and/or on the compounds ability to activate alpha$_{2B}$ and/or alpha$_{2C}$ adrenergic receptors in preference over alpha$_{2A}$ adrenergic receptors, several compounds of the invention are expected to be useful as analgesics to alleviate allodynia and chronic pain.

Specific Embodiments, Experimental

EXAMPLE A

Method A: Procedure for the preparation 4-(4-Chloro-indol-1-ylmethyl)-1,3-dihydro-imidazole-2-thione (Compound 1)

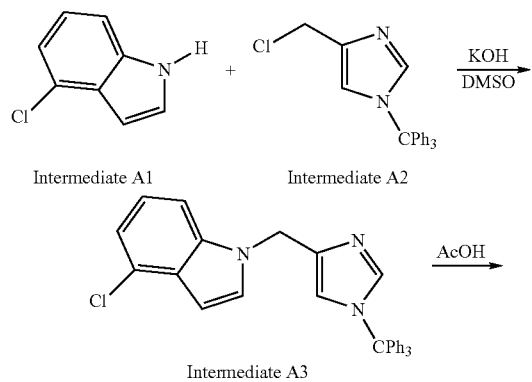

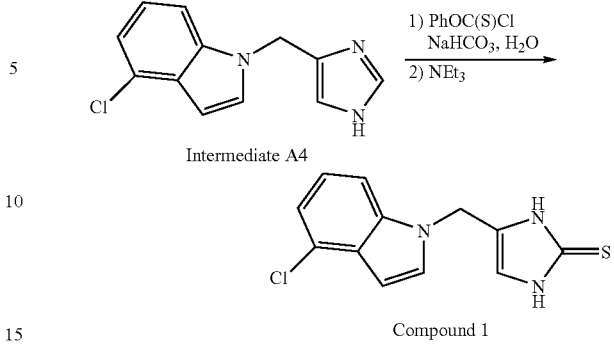

A mixture of powdered KOH (7 mmol) in DMSO (12 mL) at room temperature (rt) under N$_2$ was stirred for 0.5 h. 4-Chloro-1H-indole (Intermediate A1) (1.67 mmol) was added and the mixture was allowed to stir for 2 h at rt. The 4-chloromethyl-1-trityl-1H-imidazole (prepared according to the procedures in: James, L. K. et al; J. Med. Chem. 1997, 20, 721. and Cordi, A. A. et al Eur. J. Med. Chem. 1990, 25, 557, incorporated herein by reference) (Intermediate A2) (1.19 mmol) was added and the mixture was stirred at rt for 18 h. The solution was diluted with H$_2$O and extracted with ethyl acetate. The organic phase was washed with H$_2$O, dried over MgSO$_4$, filtered and evaporated to give the crude product. The residue was purified by chromatography on SiO$_2$ with 1-2% MeOH in CH$_2$Cl$_2$ to give 4-chloro-1-(1-trityl-1H-imidazol-4-ylmethyl)-1H-indole (Intermediate A3). The protected imidazole compound (Intermediate A3) was mixed with H$_2$O (3 mL) and acetic acid (6 mL) and heated to reflux for 1 to 2 h. The mixture was cooled to rt and made basic with 2M NaOH. The aqueous layer was extracted with ethyl acetate (2×15 mL) and the combined organic layers were dried over Na$_2$SO$_4$. This mixture was filtered, freed of solvent and purified by chromatography with 5% NH$_3$:MeOH in CH$_2$Cl$_2$ to give 4-(4-chloro-indol-1-ylmethyl)-1,3-dihydro-imidazole (Intermediate A4) (~20% over two steps).

4-(4-Chloro-indol-1-ylmethyl)-1,3-dihydro-imidazole (Intermediate A4) (0.5 mmol) in THF (3 mL) and water (3 mL) was treated with NaHCO$_3$ (5 mmol) at rt for 20 m. Phenyl chlorothionoformate (1.3 mmol) was added and stirring was continued for 4 h. The mixture was diluted with water (15 mL) and extracted with ether (3×25 mL). The organic portions were combined, dried over MgSO$_4$, filtered and the solvent was removed under vacuum. The residue was dissolved in MeOH (4 mL) and treated with NEt$_3$ (0.35 mL) for 18 h at rt. The solvent was evaporated and the product was washed on a glass frit with 50% CH$_2$Cl$_2$:hexanes to give a solid 4-(4-chloro-indol-1-ylmethyl)-1,3-dihydro-imidazole-2-thione (Compound 1) (~50%)

$^1$H NMR (300 MHz, DMSO-d$^6$ w/TMS): δ12.2 (s, 1H), 11.8 (s, 1H), 7.60 (d, J =8.7 Hz, 1H), 7.54 (d, J=3 Hz, 1H), 7.16-7.08 (m, 2H), 6.93 (brs, 1H), 6.49-6.48 (m, 1H).

EXAMPLE A-2

Compound 2

Use of 7-methyl-1H-indole (commercially available from Aldrich) in Method A produced 4-(7-methyl-indol-1-ylmethyl)-1,3-dihydro-imidazole-2-thione (Compound 2).

¹H NMR (300 MHz, DMSO-d⁶ w/TMS): δ7.38-7.33 (m, 2H), 6.92-6.83 (m, 2H), 6.43 (d, J=3.3 hz, 1H), 6.39 (s, 1H), 5.34 (s, 2H), 2.63 (s, 3H).

EXAMPLE A-3

Compound 3

Use of 7-fluoro-1H-indole (commercially available from Aldrich) in Method A produced 4-(7-fluoro-indol-1-ylmethyl)-1,3-dihydro-imidazole-2-thione (Compound 3).

¹H NMR (300 MHz, methanol-d⁴): δ7.34 (d, J=7.5 Hz, 1H), 7.27 (d, J=3.3 Hz, 1H), 7.01-6.83 (series of m, 2H), 6.64 (s, 1H), 6.53 (t, J=3.3, 1H), 5.35 (s, 2H).

EXAMPLE A-4

Compound 4

Use of 7-chloro-1H-indole (commercially available from Aldrich) in Method A produced 4-(7-chloro-indol-1-ylmethyl)-1,3-dihydro-imidazole-2-thione (Compound 4).

¹H NMR (300 MHz, DMSO-d⁶ w/TMS): δ12.2 (s, 1H), 11.9 (s, 1H), 7.54-7.51 (m, 2H), 7.15 (d, J=9 Hz, 1 H), 7.00 (t, J=7.8 Hz, 1H), 6.56 (d, J=3.3 Hz, 1H), 6.53 (s, 1H), 5.50 (s, 2H).

EXAMPLE A-5

Compound 5

Use of 7-bromo-1H-indole (commercially available from Aldrich) in Method A produced 4-(7-Bromo-indol-1-ylmethyl)-1,3-dihydro-imidazole-2-thione (Compound 5).

¹H NMR (300 MHz, DMSO-d⁶ w/TMS): δ12.1 (s, 1H), 11.9 (s, 1H), 7.57 (d, J=7.8, 1H), 7.53 (d, J=3 Hz, 1H), 7.32 (d, J=7.2 Hz, 1H), 6.95 (t, J=7.8 Hz, 1H), 6.56 (d, J=3.3 Hz, 1H), 6.50 (s, 1H), 5.56 (s, 2H).

Method B:

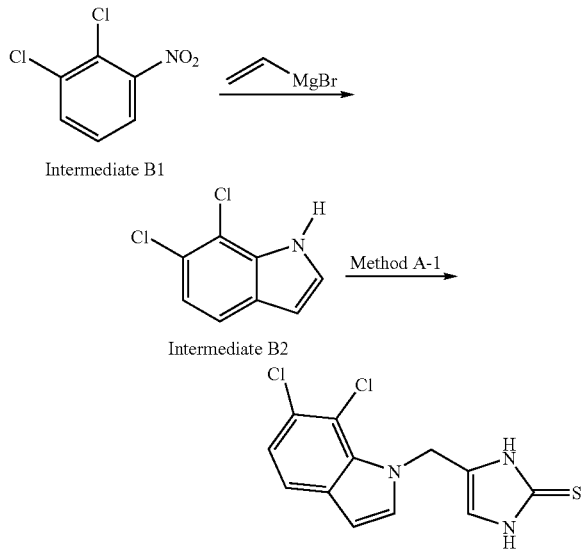

EXAMPLE B-1

Compound 6

The 6,7-dichloro-1H-indole (Intermediate B2) was synthesized by the Bartoli reaction (Bartoli, G. et al. Tetrahedron Lett. 1989, 30, 2129. 6,7-Dichloronitrobenzene (7.2 mmol) in anhydrous THF (55 mL) was treated with vinyl magnesium bromide (23 mmol, 1M solution in THF) at −45° C. After 45 m the solution was quenched with sat NH₄Cl and warmed to rt. The aqueous layer was extracted with ethyl acetate and the combined organic layers were washed with water, dried over Na₂SO₄ filtered and evaporated to give an oil. The product was purified by chromatography with 10% EtOAc:hexane to yield 6,7-dichloro-1H-indole (Intermediate B2) 52%.

4-(6,7-Dichloro-indol-1-ylmethyl)-1,3-dihydro-imidazole-2-thione (Compound 6) is prepared by substituting 6,7-dichloro-1H-indole (Intermediate B2) in Method A. (Compound 6):

¹H NMR (300 MHz, DMSO-d⁶ w/TMS) δ12.2 (s, 1H), 11.9 (s, 1H), 7.57-7.52 (m, 2H), 7.23 (d, J=7.8 Hz, 1H), 6.60-6.59 (m, 2H), 5.52 (s, 2H).

EXAMPLE B-2

Compound 7

Use of 2-chloro-3-nitro-pyridine (commercially available from Aldrich) in Method B produced 7-chloro-1H-pyrrolo[2,3-c]pyridine. Use of 7-chloro-1H-pyrrolo[2,3-c]pyridine in Method A produced 4-(7-chloro-pyrrolo[2,3-c]pyridin-1-ylmethyl)-1,3-dihydro-imidazole-2-thione (Compound 7).

¹H NMR (300 MHz, DMSO-d⁶ w/TMS) δ12.2 (s, 1H), 11.9 (s, 1H), 7.91 (d, J=5.1 Hz, 1H), 7.76 (d, J=5.1 Hz, 1H), 7.58 (d, J=5.1 Hz, 1H), 6.67-6.66 (m, 2H), 5.44 (s, 2H).

EXAMPLE C

Compound 8

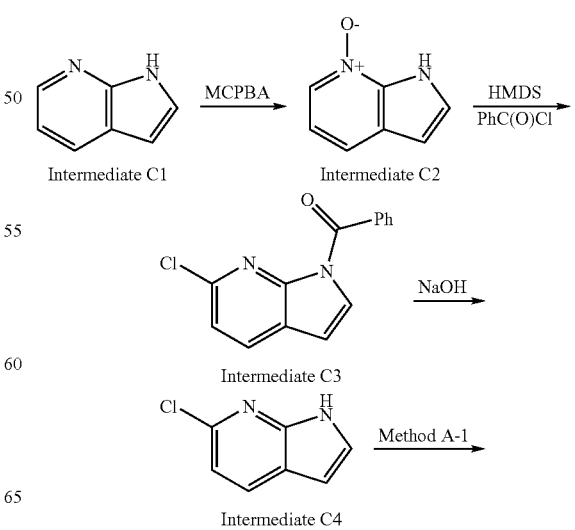

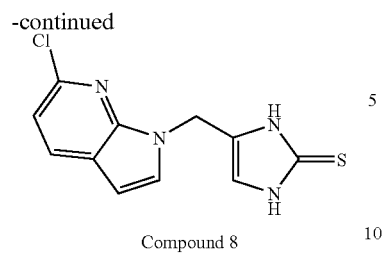

Compound 8

7-Azaindole (commercially available from Aldrich) (Intermediate C1) (31 mmol) in THF (70 mL) was reacted with MCPBA: 3-chloroperoxybenzoic acid (~35 mmol) at rt for 18 h. The solvent was removed under reduced pressure and partitioned between 2N NaOH and ethyl acetate. The product was extracted multiple times with ethyl acetate and the layers were combined, dried over $Na_2SO_4$, filtered, and reduced under vacuum. The residue was purified by column chromatography on $SiO_2$ 6% $NH_3$-MeOH in $CH_2Cl_2$ to yield 1H-pyrrolo[2,3-b]pyridine 7-oxide (Intermediate C2) (34%) (see: Minakata, S. et. aL Synthesis 1992, 661. ). 1H-pyrrolo[2,3-b]pyridine 7-oxide (Intermediate C2) (8.95 mmol) in THF (60 mL) was treated with hexamethyldisilazane (HMDS): (90 mmol) and a dropwise addition of benzoylchloride (22.5 mmol). The mixture was allowed to stir at rt for 1 h. The mixture was diluted with sat. $NaHCO_3$ and the aqueous layer extracted with ethyl acetate. The organic layers were combined, dried over $MgSO_4$, filtered and freed of solvent. The residue was purified by column chromatography (10% EtOAc:hexane) to give the product 6-chloro-pyrrolo[2,3-b]pyridin-1-yl-phenyl-methanone (Intermediate C3) as a solid.

A solution of (Intermediate C3) (3.12 mmol) in MeOH (90 mL) was treated with 1 M NaOH (30 mL) at rt for 18 h. The solution was freed of MeOH under reduced pressure and ethyl acetate was added to the aqueous layer. The aqueous layer was extracted with ethyl acetate and the combined organic layers were washed with sat. $NaHCO_3$, and dried over $Na_2SO_4$. The mixture was filtered and the solvent was evaporated to give a solid 6-chloro-1H-pyrrolo[2,3-b]pyridine (Intermediate C4).

4-(6-Chloro-pyrrolo[2,3-b]pyridin-1-ylmethyl)-1,3-dihydro-imidazole-2-thione (Compound 8) is prepared by substituting 6-chloro-1H-pyrrolo[2,3-b]pyridine in Method A. (Compound 8):

$^1$H NMR (300 MHz, DMSO-d$^6$ w/TMS) δ12.2 (s, 1H), 11.9 (s, 1H), 8.03 (d, J=8.1 Hz, 1H), 7.56 (d, J=3.6 Hz, 1H), 7.16 (d, J=13.5 Hz, 1H), 6.75 (s, 1H), 6.55 (d, J=3.6 Hz, 1H), 5.18 (s, 2H).

EXAMPLE D

Method D: Procedure for the preparation 4-[1-(6-methyl-pyridin-2-yl)-ethyl]-1,3-dihydro-imidazole-2-thione (Compound 9)

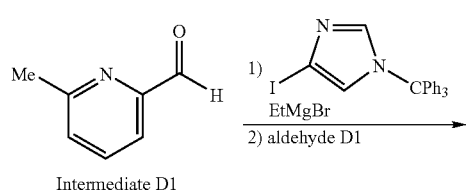

Intermediate D1

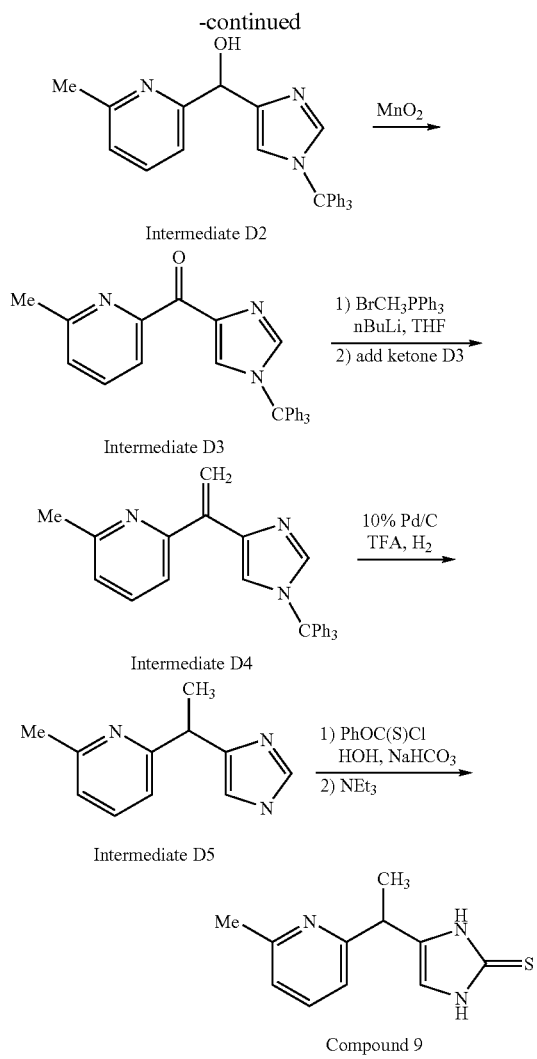

A mixture of 4-iodo-1-tritylimidazole (commercially available) (5.0 g, 11.5 mmol) in dichloromethane (50 mL) at −10° C. was treated with ethyl magnesium bromide (3.8 mL, 11.5 mmol, 3M in ether) and allowed to react for 90 m. A solution of 6-methyl-pyridine-2-carbaldehyde (Intermediate D1) (commercially available from Aldrich) (0.93 g, 7.7 mmol) in dichloromethane (10 mL) was added via syringe at −10° C. and stirred for 45 m. The mixture was quenched with water (50 mL) and with a saturated solution of ammonium chloride (60 mL). The residue was isolated in an aqueous workup, extracting with $CHCl_3$ and purified by chromatography on silica gel with 5% $NH_3$-MeOH:$CH_2Cl_2$ to give (6-Methyl-pyridin-2-yl)-(1-trityl-1H-imidazol-4-yl)-methanol (Intermediate D2) as a solid, 3.3 g (~99%).

A solution of (6-methyl-pyridin-2-yl)-(1-trityl-1H-imidazol-4-yl)-methanol (Intermediate D2) (3.7 g, 8.5 mmol) in dioxane (75 mL) was treated with activated manganese(IV) oxide ($MnO_2$), (commercially available from Aldrich): (7 g, ~80 mmol) at 90° C. for 20 m. The mixture was filtered through Celite and the solvent was removed under vacuum. The product, (6-methyl-pyridin-2-yl)-(1-trityl-1H-imidazol-4-yl)-methanone (Intermediate D3) was used in the next step without further purification 3.6 g.

Methyl triphenylphosphine bromide (commercially available from Aldrich) (2.2 g, 6.16, mmol) in THF (60 mL) at −70° C. was treated with nBuLi (2.44 mL, 2.5M in hexane). The reaction mixture warmed to −50° C. in 1 h. A solution of (6-methyl-pyridin-2-yl)-(1-trityl-1H-imidazol-4-yl)-methanone (Intermediate D3) (1.38 g, 3.2 mmol) in THF (25 mL) was added to the mixture via syringe at −50° C. The mixture was allowed to warm to rt for 1.5 h. The mixture was poured into ether (mL) and washed with water (2×10 mL). The organic solution was dried over MgSO₄, filtered and evaporated to leave a residue. This was purified by chromatography on SiO₂ with diethyl ether to give 2-methyl-6-[1-(1-trityl-1H-imidazol-4-yl)-vinyl]-pyridine (Intermediate D4) 0.68 g (50%).

A mixture of 2-methyl-6-[1-(1-trityl-1H-imidazol-4-yl)-vinyl]-pyridine (Intermediate D4) (460 mg, 1.1 mmol) in trifluoroacetic acid (TFA) (25 mL) was reduced by the action of 10% Pd/C (100 mg) under H₂ at 35 psi for 20 h at rt. The mixture was filtered through Celite and freed of solvent under reduced pressure. The residue was purified by chromatography on silica gel with 5% NH₃-MeOH:CH₂Cl₂ to give 2-[1-(1H-imidazol-4-yl)-ethyl]-6-methyl-pyridine (Intermediate D5) as a solid, 150 mg (93%).

A mixture of 2-[1-(1H-imidazol-4-yl)-ethyl]-6-methyl-pyridine (Intermediate D5) (150 mg, 0.80 mmol) in THF (8 mL) and water (8 mL) was treated with NaHCO₃ (240 mg, 2.86 mmol) and phenylchlorothionoformate (0.35 mL, 2.60 mmol) for 3 h at rt. The mixture was diluted with diethyl ether (35 mL) and water (10 mL). The aqueous layer was removed and extracted with ether (2×10 mL). The organic layers were combined, dried over MgSO₄, filtered and concentrated under vacuum. The residue was treated with triethylamine (1 mL) in methanol (9 mL) at rt for 16 h. The solvent was removed and the product was isolated and purified either by tituration with CH₂Cl₂: hexane or by chromatography on SiO₂ with EtOAc or 3 to 7% NH₃-MeOH:CH₂Cl₂. This gave 4-[1-(6-methyl-pyridin-2-yl)-ethyl]-1,3-dihydro-imidazole-2-thione (Compound 9)

50 mg (30%). ¹H NMR (300 MHz, DMSO-d⁶ w/TMS) δ11.9 (s, 1H), 11.7 (s, 1H), 7.60 (t, J=7.5 Hz, 1H), 7.07 (d, J=7.5 Hz, 1H), 7.02 (d, J=7.5 Hz, 1H), 6.53 (s, 1H), 3.95 (q, J=6.9 Hz, 1H), 2.42 (s, 3H), 1.46 (d, J=7.2 Hz, 3H).

EXAMPLE E

Method E: Procedure for the Preparation of 4-thiophen-2-ylmethyl-1,3-dihydro-imidazole-2-thione (Compound-10)

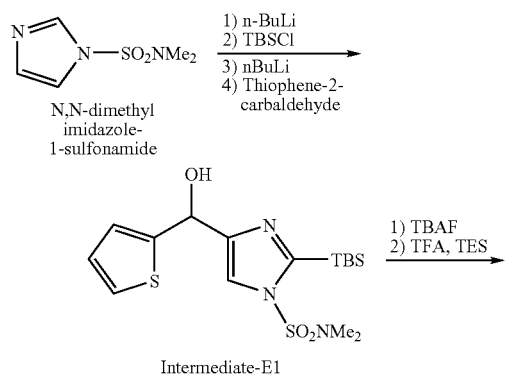

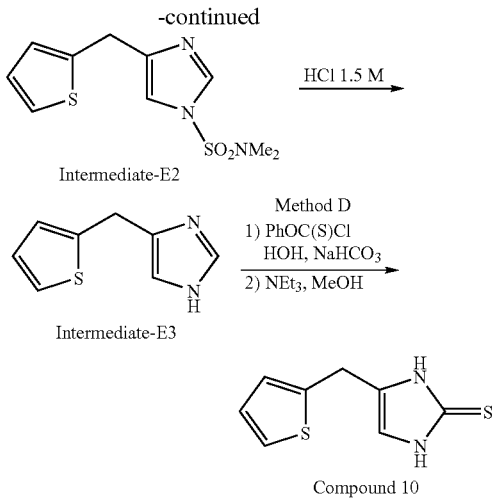

A solution of N,N-dimethyl imidazole-1-sulfonamide (commercially available from Aldrich) (1.5 g, 8.57 mmol) in THF (35 mL) at −78° C. was treated with nBuLi (5.4 mL of a 1.6 M soln) for 1 h. Solid TBSCl: tert-butyldimethylsilyl chloride (1.29 g, 8.6 mmol) in THF (5 mL) was added at rt for 16 h. The mixture was cooled to −20° C. and treated with nBuLi (5.9 mL of a 1.6 M soln) for 1 h. Thiophene-2-carbaldehyde (commercially available from Aldrich) (0.96 mL, 10.3 mmol) in THF (10 mL) is added and the mixture was stirred for 3 h at rt. The mixture was washed with brine and dried over Na₂SO₄. The solvent was removed under vacuum and the residue was purified by chromatography on silical gel with 30% EtOAc: hexane to give 2-(tert-butyl-dimethyl-silanyl)-4-(hydroxy-thiophen-2-yl-methyl)-imidazole-1-sulfonic acid dimethylamide (Intermediate-E1) 2.5 g.

2-(tert-butyl-dimethyl-silanyl)-4-(hydroxy-thiophen-2-yl-methyl)-imidazole-1-sulfonic acid dimethylamide (Intermediate-E1) (2.5 g, 6.2 mmol) in THF (60 mL) was treated with tetrabutylammonium fluoride (TBAF) (6.9 mL of a 1M soln) at 0° C. for 1 h and at rt for 3 h. The reaction mixture was subjected to an aqueous work-up and the product was purified by chromatography on silica gel with EtOAc to give 4-(hydroxy-thiophen-2-yl-methyl)-imidazole-1-sulfonic acid dimethylamide as a white solid, 1.43 g. 4-(Hydroxy-thiophen-2-yl-methyl)-imidazole-1-sulfonic acid dimethylamide (0.5 g, 1.74 mmol) in dichloromethane (25 mL) was reacted with trifluoroacetic acid (4.3 mL, 56 mmol) and triethylsilane (TES) (2.2 mL, 14 mmol) at rt for 18 h. The mixture was quenched with water and solid NaHCO₃. This material was subjected to an aqueous work-up and the residue was purified by chromatography on silica gel with 50% EtOAc: hexane to yield 4-thiophen-2-ylmethyl-imidazole-1-sulfonic acid dimethylamide (Intermediate-E2) 0.44 g.

A solution of 4-thiophen-2-ylmethyl-imidazole-1-sulfonic acid dimethylamide (Intermediate-E2) (0.44 g) in 1.5 M HCl (10 mL) was heated to reflux for 3 h. The mixture was cooled to rt and basified with NaOH solution; The mixture was extracted with ethyl acetate (2×) and the organic solution was dried over Na₂SO₄, filtered and evaporated to give 4-thiophen-2-ylmethyl-1H-imidazole (Intermediate-E3) as a white solid ~0.2 g.

4-Thiophen-2-ylmethyl-1H-imidazole (Intermediate-E3) was subjected to the appropriate process steps in Method A to produce 4-thiophen-2-ylmethyl-1,3-dihydro-imidazole-2-thione (Compound 10).

$^1$H NMR (500 MHz, DMSO-d$^6$ w/TMS): δ12.0 (s, 1H), 11.7 (s, 1H), 7.35 (d, J=5.0 Hz, 1H), 6.96-6.93 (m, 2H), 6.61 (s, 1H), 3.91 (s, 2H).

EXAMPLE F

Method F: Procedure for the Preparation of 4-(3,4-Dihydro-2H-quinolin-1-ylmethyl)-1,3-dihydro-imidazole-2-thione (Compound-11)

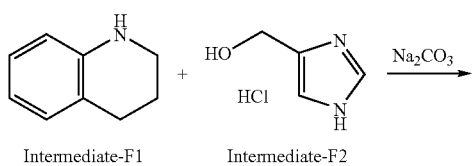

Intermediate-F1    Intermediate-F2

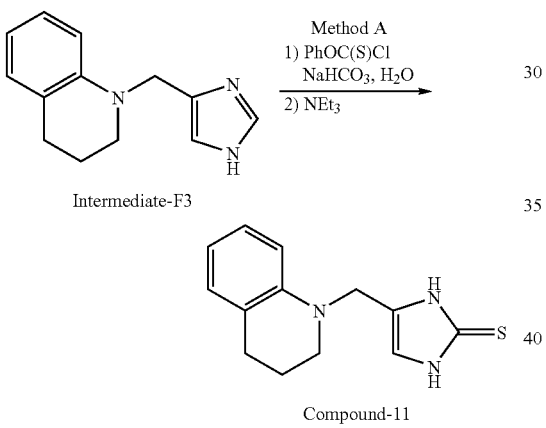

A mixture of 1,2,3,4-tetrahydro-quinoline (Intermediate F1) (Commercially available from Aldrich) (1.62 mL, 12.6 mmol) and 4-hydroxymethyl-imidazole hydrochloride salt (commercially available from Aldrich) (Intermediate F2) (0.70 g, 5.1 mmol) and sodium carbonate (1.6 g, 15.1 mmol) in water (20 mL) and dioxane (10 mL) were heated at reflux for 24 h. The mixture was cooled to rt and extracted with ethyl acetate. The organic solution was dried over MgSO$_4$, filtered and freed of solvent. The resultant oil was purified by chromatography on silica gel with 5% NH$_3$-MeOH: dichloromethane to give 1-(1H-imidazol-4-ylmethyl)-1,2,3,4-tetrahydro-quinoline (Intermediate F3) as a solid, 0.54 g (50%).

1-(1H-Imidazol-4-ylmethyl)-1,2,3,4-tetrahydro-quinoline (Intermediate F3) was subjected to the appropriate process steps in Method A to produce 4-(3,4-dihydro-2H-quinolin-1-ylmethyl)-1,3-dihydro-imidazole-2-thione (Compound 11).

$^1$H NMR (300 MHz, DMSO-d$^6$): δ12.0 (s, 1H), 11.8 (s, 1H), 6.93 (t, J=6.9 Hz, 1H), 6.87 (d, J=7.2 Hz, 1H), 6.66-6.63 (m, 1H), 6.63 (s, 1H), 6.50 (t, J=6.9 Hz, 1H), 4.18 (s, 2H), 3.28 (t, J=6.3 Hz, 2H), 2.67 (t, J=6.3 Hz, 2H), 1.90-1.84 (m, 2H).

EXAMPLE G

Method G: Procedure for the Preparation of 4-[1-(5,6,7,8-tetrahydro-quinolin-4-yl)-ethyl]-1,3-dihydro-imidazole-2-thione (Compound-12)

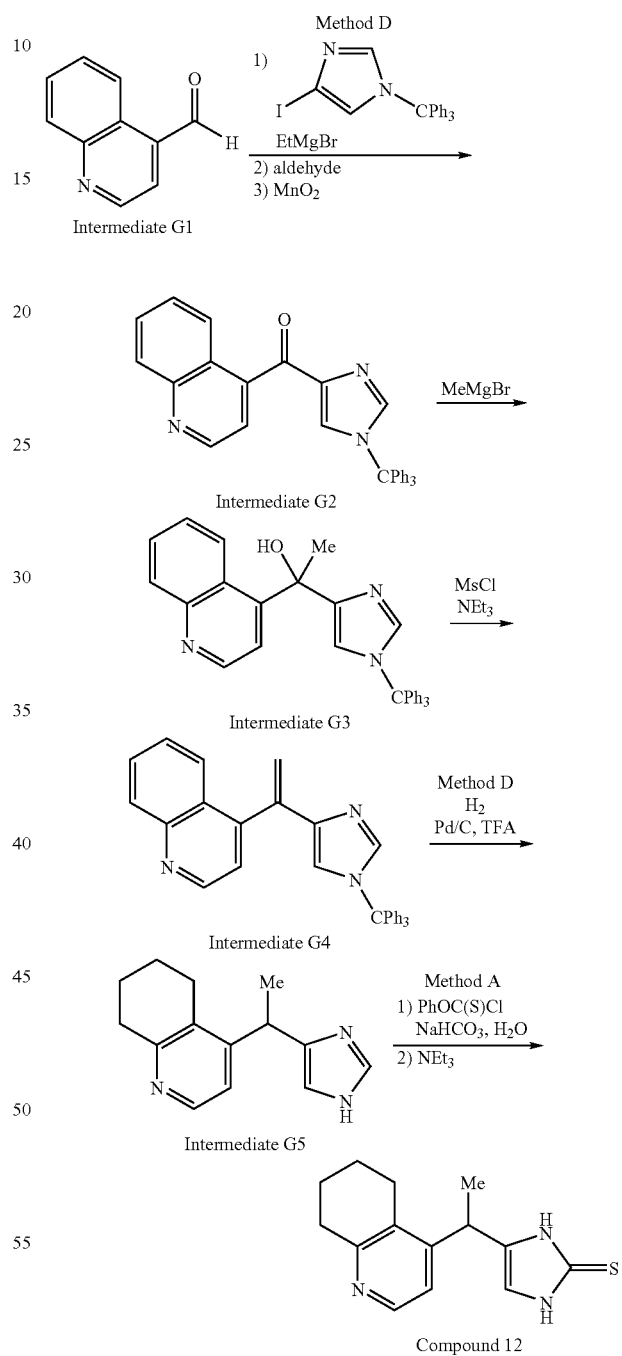

Quinoline-4-carbaldehyde (Intermediate G1) (commercially available from Aldrich) was subjected to the appropriate process steps in Method D to produce quinolin-4-yl-(1-trityl-1H-imidazol-4-yl)-methanone (Intermediate G2).

A solution of quinolin-4-yl-(1-trityl-1H-imidazol-4-yl)-methanone (Intermediate G2) (13.1 mmol) in THF (100 mL)

at 0° C. was treated with MeMgBr (9.0 mL, 27 mmol of a 3M solution in Et$_2$O) for 45 m. The mixture was quenched with a sat. solution of NH$_4$Cl and water. The layers were separated and the organic layer dried over MgSO$_4$. The suspension was filtered and evaporated to dryness. The material was purified by chromatography on SiO$_2$ with 50% EtOAc:hexane to 5% NH$_3$-MeOH: dichloromethane to give 1-quinolin-4-yl-1-(1-trityl-1H-imidazol-4-yl)-ethanol (Intermediate G3) 5.69 g.

1-Quinolin-4-yl-1-(1-trityl-1H-imidazol-4-yl)-ethanol (Intermediate G3) (4.78 g, 9.93 mmol) in dichloromethane (100 mL) was treated with triethylamine (11.0 mL, 78.9 mmol) at 0° C. Methanesulfonyl chloride (MsCL) (2.3 mL, 29.7 mmol) was added via syringe and the mixture was stirred for 2 h. (see procedure found in Toshima, K et al J Amer. Chem. Soc. 1995 117, 10825; incorporated herein by reference). The mixture was subjected to a typical aqueous work-up. The crude material was purified by chromatography on silica gel with 2% NH$_3$-MeOH: dichloromethane to give 4-[1-(1-trityl-1H-imidazol-4-yl)-vinyl]-quinoline (Intermediate G4) as a tan solid, 3.51 g (76%).

4-[1-(1-Trityl-1H-imidazol-4-yl)-vinyl]-quinoline (Intermediate G4) was subjected to the catalytic reduction procedure of Method D to produce 4-[1-(1H-imidazol-4-yl)-ethyl]-5,6,7,8-tetrahydro-quinoline (Intermediate G5). Intermediate G5 was subjected to the appropriate process steps in Method A to produce 4-[1-(5,6,7,8-tetrahydro-quinolin-4-yl)-ethyl]-1,3-dihydro-imidazole-2-thione (Compound 12)

$^1$H NMR (300 MHz, methanol-d$^4$): δ8.18 (d, J=5.1 Hz, 1H), 6.95 (d, J=5.4Hz, 1H), 6.60 (s, 1H), 4.28 (q, J=7.2 Hz, 1H), 2.88-2.76 (m, 4H), 1.89-1.86 (m, 4H), 1.48 (d, J=6.9 Hz, 3H).

EXAMPLE H

Method H: Procedure for the Preparation of 4-(1-isoquinolin-1-yl-ethyl)-1,3-dihydro-imidazole-2-thione (Compound-13)

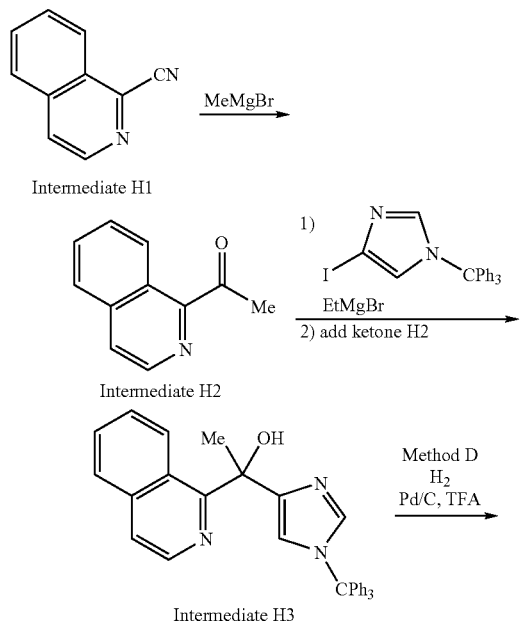

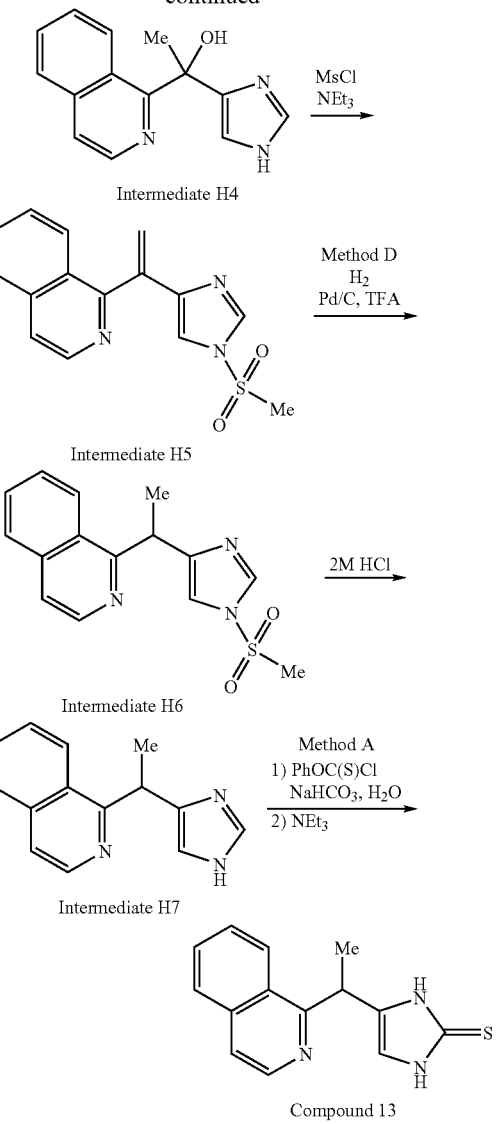

A solution of isoquinoline-1-carbonitrile (Intemediate H1) (commercially available from Aldrich) (4.40 g, 28.5 mmol) in THF at 0° C. was treated with methylmagnesium bromide (20 mL, of a 3M soln in ether) for 3 h. (see procedure found in Vacher, B. et al J. Med. Chem. 1998 41, 5070; incorporated herein by reference). The mixture was quenched with a sat. solution of NH$_4$Cl and stirred for 3 h at rt. The aqueous layer was basified with NaOH and extracted with ethyl acetate. The organic layers were dried over MgSO$_4$, filtered and concentrated under reduced pressure. The material was purified by chromatography on silica gel with 10% ethyl acetate: hexane to give 1-isoquinolin-1-yl-ethanone (Intermediate H2) 3.65 g (75%).

A mixture of 4-iodo-1-tritylimidazole (commercially available) (15.5 g, 35.4 mmol) in dichloromethane (80 mL) at 20° C. was treated with ethyl magnesium bromide (12.0 mL, 36 mmol, 3M in ether) and allowed to react for 1 h. A solution of 1-isoquinolin-1-yl-ethanone (Intermediate H2) (3.65 g, 21.3 mmol) in dichloromethane (20 mL) was added via addition funnel at 20° C. and stirred for 16 h. The mixture was quenched with sat. ammonium chloride (100 mL) and diluted with dichloromethane. The residue was isolated in an aqueous workup. The product was extracted with CH₂Cl₂ and purified by chromatography on silica gel with 5% NH₃-MeOH: CH₂Cl₂ to give 1-isoquinolin-1-yl-1-(1-trityl-1H-imidazol-4-yl)-ethanol (Intermediate H3) as a solid.

1-Isoquinolin-1-yl-1-(1-trityl-1H-imidazol-4-yl)-ethanol (Intermediate H3) was subjected to TFA: trifluoroacetic acid, Pd/C under hydrogen similar to the catalytic reduction procedure of Method D to remove the trityl group and produced 1-1H-imidazol-4-yl)-isoquinolin-1-yl ethanol (Intermediate H4).

1-1H-Imidazol-4-yl)-isoquinolin-1-yl ethanol (Intermediate H4). (~21 mmol) in dichloromethane (100 mL) was treated with triethylamine (24.0 mL, 172 mmol) at 0° C. Methanesulfonyl chloride (6.1 mL, ~75 mmol) was added via syringe and the mixture was stirred for 2 h. The mixture was subjected to an aqueous work-up. The crude material was purified by chromatography on silica gel with 20% EtOAc: hexane to 5% NH₃-MeOH: dichloromethane to give 1-[1-(1-methanesulfonyl-1H-imidazol-4-yl)-vinyl]-isoquinoline (Intermediate H5) 3 g.

1-[1-(1-Methanesulfonyl-1H-imidazol-4-yl)-vinyl]-isoquinoline (Intermediate H5) was subjected to the catalytic reduction procedure found in Method D to produce 1-[1-(1-methanesulfonyl-1H-imidazol-4-yl)-ethyl]-isoquinoline (Intermediate H6).

Methanesulfonyl-1H-imidazol-4-yl)-ethyl]-isoquinoline (Intermediate H6) in ethanol and 2M HCl was heated at reflux for 18 h. The mixture was cooled to rt and basified with NaOH solid. The aqueous layer was extracted with isopropanol: chloroform (3:1). The organic fractions were dried over MgSO₄, filtered and concentrated onto silica gel. The product, 1-[1-(1H-imidazol-4-yl)-ethyl]-isoquinoline (Intermediate H7) was eluted from a column of silica gel with 3 to 5% NH₃-MeOH: CH₂Cl₂.

1-[1-(1H-Imidazol-4-yl)-ethyl]-isoquinoline (Intermediate H7) was subjected to the appropriate process steps in Method A to produce 4-(1-isoquinolin-1-yl-ethyl)-1,3-dihydro-imidazole-2-thione (Compound 13)

¹H NMR (300 MHz, DMSO-d⁶): δ11.9 (s, 1H), 11.6 (s, 1H), 8.42 (dd, J=5.4, 2.7 Hz, 1H), 8.31 (d, J=8.1 Hz, 1H), 7.96 (d, J=8.1 Hz, 1H), 7.78-7.64 (m, 3H), 6.40 (s, 1H), 5.0 (q, J=6.9 Hz, 1H), 1.59 (d, J=6.9 Hz, 3H).

Method I: Procedure for the Preparation of 4-(1-benzofuran-3-yl-ethyl)-1,3-dihydro-imidazole-2-thione (Compound-14)

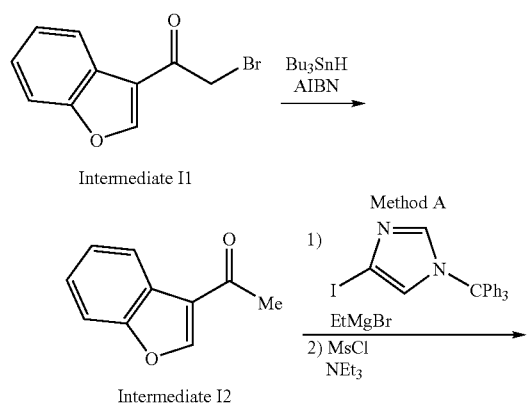

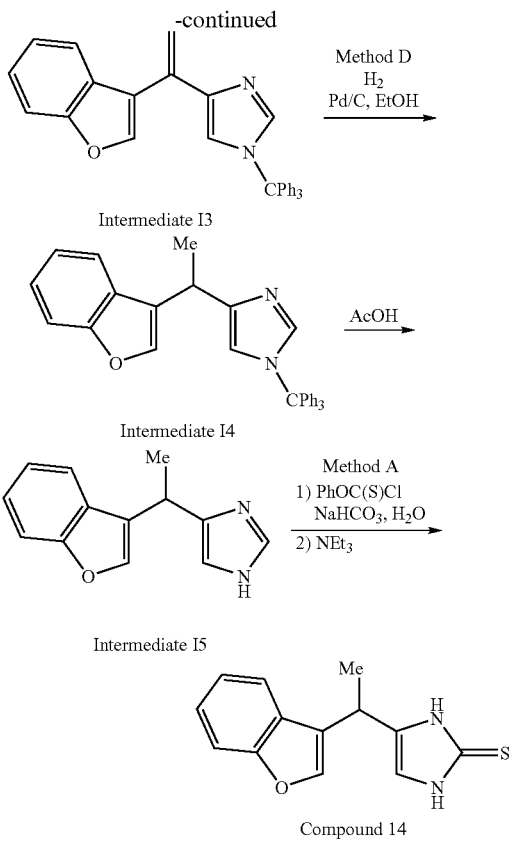

A solution of 1-benzofuran-3-yl-2-bromo-ethanone (Intermediate I1) (commercially available from Maybridge) (2.1 g, 8.8 mmol) in toluene at reflux was treated with tributyltin hydride (2.9 mL, 10.6 mmol) and 2,2'-azobisisobutyronitrile (AIBN, catalyst) for 2 h. The mixture was cooled to rt and concentrated onto silica gel under reduced pressure. The product was eluted from a column of silica gel with 5% EtOAc: hexane to give 1-benzofuran-3-yl-ethanone (Intermediate I2) as an oil, 1.45 g (99%).

1-Benzofuran-3-yl-ethanone (Intermediate I2) was treated with the appropriate process steps in Method A and Method D to produce Intermediate I3 and 4-(1-benzofuran-3-yl-ethyl)-1-trityl-1H-imidazole (Intermediate I4) respectively.

4-(1-Benzofuran-3-yl-ethyl)-1-trityl-1H-imidazole (Intermediate I4) (0.52 g) in acetic acid (10 mL) and water (5 mL) was heated to reflux for 1 h. The mixture was cooled to rt and the pH was adjusted with 2M NaOH until basic. The aqueous layer was extracted with dichloromethane. The organic layers were combined, dried over MgSO₄ and filtered through paper. The solvent was removed under a vacuum. The residue was purified by chromatography on silical gel with 2.5% NH₃-MeOH: CH₂Cl₂ to give 4-(1-benzofuran-3-yl-ethyl)-1H-imidazole Intermediate I5) 0.29 g.

4-(1-Benzofuran-3-yl-ethyl)-1H-imidazole (Intermediate I5) was subjected to the appropriate process steps in Method A to produce 4-(1-benzofuran-3-yl-ethyl)-1,3-dihydro-imidazole-2-thione (Compound I4)

¹H NMR (300 MHz, methanol-d⁴): δ7.61 (s, 1H), 7.46 (d, J=9.0 Hz, 2H), 7.27 (t, J=9.0 Hz, 1H), 7.17 (t, J=9.0 Hz, 1H), 6.60 (s, 1H), 4.22 (q, J=9.0 Hz, 1H), 1.66 (d, J=9.0 Hz, 3H).

What is claimed is:

1. A compound of general formula wherein
  m and are 1;
  q is 0;

W is N and attached directly to
X and Y represent carbons;
the dashed lines represent a bond or absence of a bond with the proviso that there are no more than 3 dashed lines present in the ring;
$R_1$ is independently H or alkyl of 1 to 4 carbons;
$R_2$ is independently H or alkyl of 1 to 4 carbons, $C(O)R_8$, carbocyclic aryl or heterocyclic aryl having 1 to 3 heteroatoms independently selected from N, O and S;
p is an integer selected from 0, 1, 2, 3, 4, and 5;
$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I and carbocyclic aryl;
$R_6$ is independently H or alkyl of 1 to 4 carbons, carbocyclic aryl or heterocyclic aryl having 1 to 3 heteroatoms independently selected from N, O and S;
$R_7$ and $R_8$ are each independently Cl, Br, F, or methyl;
Or optionally $R_7$ and $R_8$ together with the atoms to which they are attached jointly form a carbocyclic or a heterocyclic ring, the heterocyclic ring having 5 or 6 atoms in the ring and 1 to 3 heteroatoms independently selected from N, O and S; said carbocyclic or a heterocyclic ring being optionally substituted with 1 to 4 $R_9$ groups;
$R_9$ is independently selected from the groups consisting of alkyl of 1 to 4 carbons, alkenyl of 2 to 4 carbons, $CH_2OR_2$, $CH_2N(R_2)_2$, $CH_2CN$, $C(O)R_2$, $C(O)OR_6$, $SO_3R_6$, $SO_2N(R_2)_2$, $CH_2SR_2$, F, Cl, Br, I, fluoro substituted alkyl of 1 to 4 carbons, CN, $N_3$, $N(R_2)_2$, $OR_2$, $SR_2$.

2. A compound in accordance with claim 1 having the formula

3. A compound in accordance with claim 1 having the formula

4. A compound in accordance with claim 1 having the formula

5. A compound in accordance with claim 1 having the formula

6. The compound of claim 1 of the structure

-continued
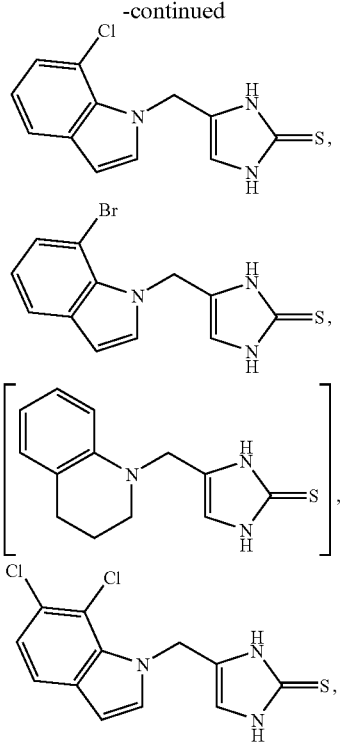
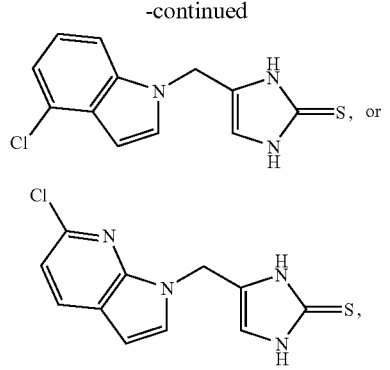
7. The compound of claim 1 wherein the ring
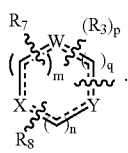
is indolyl having a single substituent.
* * * * *